United States Patent
Donovan et al.

(10) Patent No.: US 12,082,876 B1
(45) Date of Patent: Sep. 10, 2024

(54) INTRODUCER DRILL

(71) Applicant: RELIEVANT MEDSYSTEMS, INC., Minneapolis, MN (US)

(72) Inventors: Brian W. Donovan, San Jose, CA (US); Alexander Pruitt, San Jose, CA (US)

(73) Assignee: Relievant Medsystems, Inc., Minneapolis, MN (US)

( * ) Notice: Subject to any disclaimer, the term of this patent is extended or adjusted under 35 U.S.C. 154(b) by 431 days.

(21) Appl. No.: 17/449,051

(22) Filed: Sep. 27, 2021

Related U.S. Application Data

(60) Provisional application No. 63/084,381, filed on Sep. 28, 2020.

(51) Int. Cl.
*A61B 17/16* (2006.01)
*A61B 18/12* (2006.01)
(Continued)

(52) U.S. Cl.
CPC ...... *A61B 18/1492* (2013.01); *A61B 17/1615* (2013.01); *A61B 17/1642* (2013.01);
(Continued)

(58) Field of Classification Search
CPC ...... A61B 17/3472; A61B 2017/00261; A61B 17/3478; A61B 17/8805;
(Continued)

(56) References Cited

U.S. PATENT DOCUMENTS 3,054,881 A 9/1962 Metz et al.
3,062,876 A 11/1962 Pons, Jr. et al.
(Continued)

FOREIGN PATENT DOCUMENTS

AU 2001033279 2/2001
AU 2003248436 9/2003
(Continued)

OTHER PUBLICATIONS

U.S. Appl. No. 16/152,834 U.S. Pat. No. 11,471,171, filed Oct. 5, 2018, Bipolar Radiofrequencey Ablation Systems for Treatment Within Bone.
(Continued)

*Primary Examiner* — Samuel S Hanna
(74) *Attorney, Agent, or Firm* — Nelson Mullins Riley & Scarborough LLP

(57) ABSTRACT

A steerable, or curveable, introducer drill to access a target treatment region within bone along a curved trajectory is disclosed. The drill may include a drive shaft including a proximal rotational member, a distal drill tip, and an elongate shaft portion extending from the proximal rotational member to the distal drill tip. The distal drill tip may be sharp and include cutting flutes. The drill may also include an outer tube surrounding the drive shaft. A distal end portion of the outer tube may include a segmented tube section configured to facilitate controlled bending of the segmented tube section of the outer tube. The drill may also include an actuator operably coupled to the drive shaft and adapted to apply tension to the drive shaft which, in turn, causes the segmented tube section of the outer tube to bend.

16 Claims, 4 Drawing Sheets

(51) Int. Cl.
  *A61B 18/14* (2006.01)
  *A61B 17/00* (2006.01)
  *A61B 18/00* (2006.01)
(52) U.S. Cl.
  CPC .............. *A61B 18/1206* (2013.01);
    *A61B 2017/00309* (2013.01); *A61B 2017/00367* (2013.01); *A61B 2017/00455* (2013.01); *A61B 2017/00867* (2013.01); *A61B 2018/00077* (2013.01); *A61B 2018/00083* (2013.01); *A61B 2018/00202* (2013.01); *A61B 2018/00208* (2013.01); *A61B 2018/00339* (2013.01); *A61B 2018/00565* (2013.01); *A61B 2018/00946* (2013.01); *A61B 2018/00952* (2013.01); *A61B 2018/126* (2013.01)
(58) Field of Classification Search
  CPC ........ A61B 2018/0044; A61B 17/1671; A61B 17/1757; A61B 18/082; A61B 18/1487; A61B 2018/00339; A61B 2018/00565; A61B 2018/1425; A61B 17/1655; A61B 17/1659; A61B 17/32; A61B 17/3403; A61B 2010/045; A61B 18/1492; A61B 2017/00331; A61B 17/1642; A61B 18/22; A61B 2017/003; A61B 2017/00309; A61B 2017/00318; A61B 2017/00336
  See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Bom |
| 3,997,408 A | 8/1976 | MacKew |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Durate |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shalov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishibara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullett |
| 5,061,266 A | 10/1991 | Hakky |
| 5,070,879 E | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley et al. |
| 5,147,355 A | 9/1992 | Friedman et al. |
| 5,156,157 A | 10/1992 | Valenta, Jr. et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatsbabi |
| 5,226,430 A | 7/1993 | Spear et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder et al. |
| 5,282,468 A | 2/1994 | Klepinski |
| 5,292,321 A | 3/1994 | Lee |
| 5,295,484 A | 3/1994 | Marcus et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Pasafaro et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Turner et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Hamm et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,265 A | 12/1994 | Sand |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |

(56) References Cited

U.S. PATENT DOCUMENTS

| | | |
|---|---|---|
| 5,419,767 A | 5/1995 | Eggers et al. |
| 5,421,338 A | 6/1995 | Crowley |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Millis et al. |
| 5,449,380 A | 9/1995 | Chin |
| 5,454,373 A | 10/1995 | Koger et al. |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Passafaro et al. |
| 5,484,432 A | 1/1996 | Sand |
| 5,486,170 A | 1/1996 | Winston et al. |
| 5,501,703 A | 3/1996 | Holsheimer et al. |
| 5,505,730 A | 4/1996 | Edwarrds |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Fram et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Silwa, Jr. et al. |
| 5,565,005 A | 10/1996 | Erickson et al. |
| 5,569,242 A | 10/1996 | Lax et al. |
| 5,571,088 A | 11/1996 | Lennox et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Chapelon et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holshiemer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Chapelon et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Erickson et al. |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Wijkamp |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Then |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Marcove et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,374 A | 2/2000 | McDaniel |
| 6,030,402 A | 2/2000 | Thompson et al. |

(56) References Cited

U.S. PATENT DOCUMENTS

| | | |
|---|---|---|
| 6,032,673 A | 3/2000 | Langberg et al. |
| 6,032,674 A | 3/2000 | Eggers et al. |
| 6,033,411 A | 3/2000 | Preissman et al. |
| 6,035,238 A | 3/2000 | Ingle et al. |
| 6,038,480 A | 3/2000 | Hrdlicka et al. |
| 6,045,532 A | 4/2000 | Eggers et al. |
| 6,046,187 A | 4/2000 | Berde et al. |
| 6,047,214 A | 4/2000 | Mueller et al. |
| 6,050,995 A | 4/2000 | Durgin |
| 6,053,172 A | 4/2000 | Hovda et al. |
| 6,053,909 A | 4/2000 | Shadduck |
| 6,056,745 A | 5/2000 | Panescu et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Whayne et al. |
| 6,073,051 A | 6/2000 | Sharkey et al. |
| 6,074,352 A | 6/2000 | Hynynen et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sbarkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh et al. |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |

(56) References Cited

U.S. PATENT DOCUMENTS

| | | |
|---|---|---|
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,505,075 B1 | 1/2003 | Weiner |
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman, III et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckai et al. |
| 7,569,626 B2 | 8/2009 | Truckai |
| 7,574,257 B2 | 8/2009 | Rittman, III |

(56) References Cited

U.S. PATENT DOCUMENTS

| | | |
|---|---|---|
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,717,918 B2 | 5/2010 | Truckai et al. |
| 7,722,620 B2 | 5/2010 | Truckai et al. |
| 7,731,720 B2 | 6/2010 | Sand et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,780,733 B2 | 8/2010 | Carver et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,534 B2 | 2/2011 | Hamel et al. |
| 7,887,543 B2 | 2/2011 | Sand et al. |
| 7,892,235 B2 | 2/2011 | Ellis |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Malecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 | 5/2011 | Boucher et al. |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,972,340 B2 | 7/2011 | Sand et al. |
| 8,000,785 B2 | 8/2011 | Ritmann, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | McGuckin, Jr. et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,092,456 B2 | 1/2012 | Bleich et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,268 B2 | 5/2012 | Godara et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,192,442 B2 | 6/2012 | Truckai et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara et al. |
| 8,348,946 B2 | 1/2013 | McClurken et al. |
| 8,348,955 B2 | 1/2013 | Truckai et al. |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,430 B2 | 4/2013 | Pond, Jr. et al. |
| 8,425,507 B2 | 4/2013 | Pellegrino et al. |
| 8,430,881 B2 | 4/2013 | Bleich et al. |
| 8,430,887 B2 | 4/2013 | Truckai et al. |
| 8,444,636 B2 | 5/2013 | Shadduck et al. |
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |
| 8,540,723 B2 | 9/2013 | Shadduck et al. |
| 8,556,891 B2 | 10/2013 | Mathur |
| 8,556,910 B2 | 10/2013 | Truckai et al. |
| 8,556,911 B2 | 10/2013 | Mehta et al. |
| 8,560,062 B2 | 10/2013 | Rittman, III et al. |
| 8,562,598 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,088 B2 | 12/2013 | Stern et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |
| 8,747,359 B2 | 6/2014 | Pakter et al. |
| 8,747,398 B2 | 6/2014 | Behnke |
| 8,758,349 B2 | 6/2014 | Germain et al. |

(56) References Cited

U.S. PATENT DOCUMENTS

| | | |
|---|---|---|
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |
| 8,814,873 B2 | 8/2014 | Schaller et al. |
| 8,818,503 B2 | 8/2014 | Rittman, III |
| 8,821,488 B2 | 9/2014 | Stewart et al. |
| 8,828,001 B2 | 9/2014 | Stearns et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,880,189 B2 | 11/2014 | Lipani |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,616 B2 | 11/2014 | Harrison et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,521 B2 | 3/2015 | VanWyk |
| 8,992,522 B2 | 3/2015 | Pellegrino et al. |
| 8,992,523 B2 | 3/2015 | Pellegrino et al. |
| 8,992,524 B1 | 3/2015 | Ellman |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,050,109 B2 | 6/2015 | Smith |
| 9,050,112 B2 | 6/2015 | Greenhalgh et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schutlz et al. |
| 9,113,974 B2 | 8/2015 | Germain |
| 9,119,623 B2 | 9/2015 | Malis et al. |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,047 B2 | 10/2015 | To et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,216,195 B2 | 12/2015 | Truckai et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,479 B2 | 3/2016 | Hibri et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,373 B2 | 6/2016 | Smith |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |

(56) References Cited

U.S. PATENT DOCUMENTS

| | | |
|---|---|---|
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,057 B2 | 8/2016 | Germain |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Banamou et al. |
| 9,532,828 B2 | 1/2017 | Condie et al. |
| 9,545,283 B2 | 1/2017 | Sack et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,108 B2 | 2/2017 | Brustad et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,675,408 B2 | 6/2017 | Godara et al. |
| 9,681,889 B1 | 6/2017 | Greenhalgh et al. |
| 9,687,255 B2 | 6/2017 | Sennett et al. |
| 9,717,551 B2 | 8/2017 | Krueger et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,750,570 B2 | 9/2017 | Condie et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,826,985 B2 | 11/2017 | Slobitker et al. |
| 9,844,406 B2 | 12/2017 | Edwards et al. |
| 9,848,890 B2 | 12/2017 | Yoon et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,901,392 B2 | 2/2018 | Phan et al. |
| 9,913,675 B2 | 3/2018 | Germain |
| 9,918,786 B2 | 3/2018 | Wang et al. |
| 9,980,771 B2 | 5/2018 | Carter et al. |
| 9,993,285 B2 | 6/2018 | Govari et al. |
| 10,022,140 B2 | 7/2018 | Germain et al. |
| 10,028,753 B2 | 7/2018 | Pellegrino et al. |
| 10,028,784 B2 | 7/2018 | Kramer et al. |
| 10,052,149 B2 | 8/2018 | Germain et al. |
| 10,052,152 B2 | 8/2018 | Tegg et al. |
| 10,052,153 B2 | 8/2018 | Olson |
| 10,058,336 B2 | 8/2018 | Truckai et al. |
| 10,105,175 B2 | 10/2018 | Godara et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,159,497 B2 | 12/2018 | Kuntz et al. |
| 10,245,092 B2 | 4/2019 | Germain |
| 10,265,099 B2 | 4/2019 | Pellegrino et al. |
| 10,272,271 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,314,633 B2 | 6/2019 | Linderman et al. |
| 10,327,841 B2 | 6/2019 | Germain |
| 10,357,258 B2 | 7/2019 | Patel et al. |
| 10,357,307 B2 | 7/2019 | Harrison et al. |
| 10,376,271 B2 | 8/2019 | Mehta et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,441,354 B2 | 10/2019 | Govari et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,582,966 B2 | 3/2020 | Orczy-Timko et al. |
| 10,588,691 B2 | 3/2020 | Pellegino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,835,234 B2 | 11/2020 | Harari et al. |
| 10,849,613 B2 | 12/2020 | Rosner et al. |
| 10,864,040 B2 | 12/2020 | Dastjerdi et al. |
| 10,898,254 B2 | 1/2021 | Diederich et al. |
| 10,905,440 B2 | 2/2021 | Pellegrino et al. |
| 10,918,363 B2 | 2/2021 | Godara et al. |
| RE48,460 E | 3/2021 | Pellegrino et al. |
| 10,952,771 B2 | 3/2021 | Pellegrino |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 | 7/2021 | Edidin |
| 11,116,570 B2 | 9/2021 | Purdy et al. |
| 11,123,103 B2 | 9/2021 | Donovan et al. |
| 11,147,684 B2 | 10/2021 | Neubardt |
| 11,160,503 B2 | 11/2021 | Peesapati et al. |
| 11,160,563 B2 | 11/2021 | Patel et al. |
| 11,166,747 B2 | 11/2021 | Brockman et al. |
| 11,191,575 B2 | 12/2021 | Kidman et al. |

(56) References Cited

U.S. PATENT DOCUMENTS

| | | |
|---|---|---|
| 11,207,100 B2 | 12/2021 | Donovan et al. |
| 11,224,475 B2 | 1/2022 | Godara et al. |
| 11,234,764 B1 | 2/2022 | Patel et al. |
| 11,259,818 B2 | 3/2022 | Brockman et al. |
| 11,291,502 B2 | 4/2022 | Patel et al. |
| 11,344,350 B2 | 5/2022 | Purdy et al. |
| 11,364,069 B2 | 6/2022 | Heggeness |
| 11,376,021 B2 | 7/2022 | Marino et al. |
| 11,389,181 B2 | 7/2022 | Dutertre et al. |
| 11,419,614 B2 | 8/2022 | Weitzman et al. |
| 11,426,199 B2 | 8/2022 | Donovan et al. |
| 11,471,171 B2 | 10/2022 | Pellegrino et al. |
| 11,471,210 B2 | 10/2022 | Pellegrino et al. |
| 11,497,543 B2 | 11/2022 | Sprinkle et al. |
| 11,510,723 B2 | 11/2022 | Defosset et al. |
| 11,596,468 B2 | 3/2023 | Pellegrino et al. |
| 11,690,667 B2 | 7/2023 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hovda et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016583 A1 | 2/2002 | Cragg |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0052600 A1 | 5/2002 | Davison et al. |
| 2002/0068930 A1 | 6/2002 | Tasto et al. |
| 2002/0095144 A1 | 7/2002 | Carl |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1 | 9/2002 | Daniel et al. |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0183758 A1 | 12/2002 | Middleton et al. |
| 2002/0188284 A1 | 12/2002 | To et al. |
| 2002/0188290 A1 | 12/2002 | Sharkey et al. |
| 2002/0193708 A1 | 12/2002 | Thompson et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0040710 A1 | 2/2003 | Polidoro |
| 2003/0040742 A1 | 2/2003 | Underwood et al. |
| 2003/0040743 A1 | 2/2003 | Cosman et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |
| 2004/0064136 A1 | 4/2004 | Crombie et al. |
| 2004/0064137 A1 | 4/2004 | Pellegrino et al. |
| 2004/0068242 A1 | 4/2004 | McGuckin, Jr. |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120668 A1 | 6/2004 | Loeb |
| 2004/0120891 A1 | 6/2004 | Hill et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0193152 A1 | 9/2004 | Sutton et al. |
| 2004/0220577 A1 | 11/2004 | Cragg et al. |
| 2004/0225228 A1 | 11/2004 | Ferree |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209610 A1 | 9/2005 | Carrison |
| 2005/0209659 A1 | 9/2005 | Pellegrino et al. |
| 2005/0216018 A1 | 9/2005 | Sennett |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0036264 A1 | 2/2006 | Selover et al. |
| 2006/0052743 A1 | 3/2006 | Reynolds |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |
| 2006/0276749 A1 | 12/2006 | Selmon et al. |
| 2006/0287649 A1 | 12/2006 | Ormsby et al. |
| 2007/0021803 A1 | 1/2007 | Deem et al. |
| 2007/0027449 A1 | 2/2007 | Godara et al. |

(56) References Cited

U.S. PATENT DOCUMENTS

| | | |
|---|---|---|
| 2007/0055316 A1 | 3/2007 | Godara et al. |
| 2007/0066987 A1 | 3/2007 | Scanlan et al. |
| 2007/0074719 A1 | 4/2007 | Danek et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149846 A1 | 6/2009 | Hoey et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0286487 A1 | 11/2010 | Van Lue |
| 2010/0298737 A1 | 11/2010 | Koehler |
| 2010/0298822 A1 | 11/2010 | Behnke |
| 2010/0298832 A1 | 11/2010 | Lau et al. |
| 2010/0305559 A1 | 12/2010 | Brannan et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0152855 A1 | 6/2011 | Mayse et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0270238 A1 | 11/2011 | Rizq et al. |
| 2011/0276001 A1 | 11/2011 | Schultz et al. |
| 2011/0295245 A1 | 12/2011 | Willyard et al. |
| 2011/0295261 A1 | 12/2011 | Germain |
| 2011/0319765 A1 | 12/2011 | Gertner et al. |
| 2012/0029420 A1 | 2/2012 | Rittman et al. |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0143341 A1 | 6/2012 | Zipnick |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226145 A1 | 9/2012 | Chang et al. |
| 2012/0226273 A1 | 9/2012 | Nguyen et al. |
| 2012/0239049 A1 | 9/2012 | Truckai et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0103022 A1 | 4/2013 | Sutton et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0324993 A1 | 12/2013 | McCarthy et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1* | 10/2014 | Burger .............. A61B 17/8855 606/80 |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |

(56) References Cited

U.S. PATENT DOCUMENTS

| | | |
|---|---|---|
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0296739 A1 | 10/2016 | Burdick et al. |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0246481 A1 | 8/2017 | Mishelevich |
| 2017/0266419 A1 | 9/2017 | Gosbayeshgar |
| 2017/0303983 A1 | 10/2017 | Linderman et al. |
| 2017/0312007 A1 | 11/2017 | Harlev et al. |
| 2017/0333052 A1 | 11/2017 | Ding et al. |
| 2018/0021048 A1 | 1/2018 | Pellegrino et al. |
| 2018/0042656 A1 | 2/2018 | Edidin |
| 2018/0055539 A1 | 3/2018 | Pellegino |
| 2018/0103964 A1 | 4/2018 | Patel et al. |
| 2018/0140245 A1 | 5/2018 | Videman |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2018/0303509 A1 | 10/2018 | Germain et al. |

(56) References Cited

U.S. PATENT DOCUMENTS

| | | |
|---|---|---|
| 2019/0029698 A1 | 1/2019 | Pellegrino et al. |
| 2019/0038296 A1 | 2/2019 | Pellegrino |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0216486 A1 | 7/2019 | Weitzman |
| 2019/0282268 A1 | 9/2019 | Pellegrino et al. |
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Alambeigi et al. |
| 2020/0022709 A1 | 1/2020 | Burger et al. |
| 2020/0022749 A1 | 1/2020 | Malkevich et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0179033 A1 | 6/2020 | Banamou et al. |
| 2020/0214762 A1 | 7/2020 | Pellegrino et al. |
| 2020/0281646 A1 | 9/2020 | Pellegrino et al. |
| 2020/0390493 A1 | 12/2020 | Orczy-Timko et al. |
| 2020/0405499 A1 | 12/2020 | Gerbec et al. |
| 2021/0022814 A1 | 1/2021 | Crawford et al. |
| 2021/0077170 A1 | 3/2021 | Wiersdorf et al. |
| 2021/0093373 A1 | 4/2021 | Dastjerdi et al. |
| 2021/0113238 A1 | 4/2021 | Donovan et al. |
| 2021/0145416 A1 | 5/2021 | Godara et al. |
| 2021/0177502 A1 | 6/2021 | Wright et al. |
| 2021/0290254 A1 | 9/2021 | Serrahima Tornel et al. |
| 2021/0361350 A1 | 11/2021 | Pellegrino et al. |
| 2021/0361351 A1 | 11/2021 | Pellegrino et al. |
| 2021/0369323 A1 | 12/2021 | Edidin |
| 2021/0386491 A1 | 12/2021 | Shmayahu et al. |
| 2021/0401496 A1 | 12/2021 | Purdy et al. |
| 2022/0022930 A1 | 1/2022 | Brockman et al. |
| 2022/0031390 A1 | 2/2022 | Ebersole et al. |
| 2022/0096143 A1 | 3/2022 | Godara et al. |
| 2022/0110639 A1 | 4/2022 | Brockman et al. |
| 2022/0192702 A1 | 6/2022 | Donovan |
| 2022/0192722 A1 | 6/2022 | Harshman et al. |
| 2022/0202471 A1 | 6/2022 | Schepis et al. |
| 2022/0218411 A1 | 7/2022 | Druma et al. |
| 2022/0218434 A1 | 7/2022 | Druma |
| 2022/0240916 A1 | 8/2022 | Jung et al. |
| 2022/0296255 A1 | 9/2022 | Patel et al. |
| 2022/0401114 A1 | 12/2022 | Marino et al. |
| 2023/0046328 A1 | 2/2023 | Weitzman et al. |
| 2023/0138303 A1 | 5/2023 | Pellegrino |
| 2023/0172656 A1 | 6/2023 | Druma |
| 2023/0255676 A1 | 8/2023 | Donovan et al. |

FOREIGN PATENT DOCUMENTS

| | | |
|---|---|---|
| AU | 2008249202 | 9/2003 |
| AU | 2011218612 | 9/2003 |
| AU | 2009296474 | 9/2009 |
| AU | 2015234376 | 9/2009 |
| AU | 2018223007 | 9/2009 |
| AU | 20112044278 | 1/2010 |
| AU | 2011204278 | 1/2011 |
| AU | 2012362524 | 12/2012 |
| AU | 2013337680 | 11/2013 |
| AU | 2012244378 B2 | 5/2015 |
| AU | 2019201705 | 3/2019 |
| AU | 2019206037 | 7/2019 |
| AU | 2020201962 | 3/2020 |
| AU | 2021200382 | 1/2021 |
| AU | 2020346827 | 3/2022 |
| AU | 2021306313 | 1/2023 |
| AU | 2023204019 | 6/2023 |
| AU | 2021409967 | 7/2023 |
| AU | 2022239314 | 9/2023 |
| CA | 2397413 | 2/2001 |
| CA | 2723071 | 2/2001 |
| CA | 2443491 | 9/2003 |
| CA | 2737374 | 9/2009 |
| CA | 2957010 | 9/2009 |
| CA | 2785207 | 1/2011 |
| CA | 2889478 | 11/2013 |
| CA | 28589478 | 11/2013 |
| CA | 3093398 | 9/2020 |
| CA | 3150339 | 3/2022 |
| CA | 3202650 | 6/2023 |
| CA | 3211365 | 9/2023 |
| EP | 0040658 | 12/1981 |
| EP | 0584959 | 3/1994 |
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 1905397.4 | 2/2001 |
| EP | 7010394 | 2/2001 |
| EP | 7010581.2 | 2/2001 |
| EP | 7010649.7 | 2/2001 |
| EP | 10012521 | 2/2001 |
| EP | 16197060.3 | 2/2001 |
| EP | 3256168 | 9/2003 |
| EP | 5021597.9 | 9/2003 |
| EP | 10012523.6 | 9/2003 |
| EP | 1294323 B1 | 4/2007 |
| EP | 1938765 A1 | 7/2008 |
| EP | 9816892.5 | 9/2009 |
| EP | 1471836 B1 | 4/2010 |
| EP | 1732213.1 | 1/2011 |
| EP | 11732213.1 | 1/2011 |
| EP | 13852217.2 | 11/2013 |
| EP | 2785260 | 8/2015 |
| EP | 2965782 | 1/2016 |
| EP | 2508225 | 9/2016 |
| EP | 3078395 | 10/2016 |
| EP | 2205313 B1 | 11/2016 |
| EP | 3097946 | 11/2016 |
| EP | 2913081 | 1/2017 |
| EP | 18166323.8 | 4/2018 |
| EP | 19162385.9 | 3/2019 |
| EP | 20161054.0 | 3/2020 |
| EP | 20862138.3 | 3/2022 |
| EP | 22771962.2 | 9/2023 |
| HK | 8102841.9 | 2/2001 |
| HK | 8103900.5 | 2/2001 |
| HK | 17108246.6 | 2/2001 |
| HK | 12100034.4 | 9/2009 |
| HK | 13105656.9 | 1/2011 |
| HK | 16100183.9 | 11/2013 |
| HK | 161002183.9 | 11/2013 |
| HK | 19124269.2 | 5/2019 |
| IL | 220747 | 1/2011 |
| IL | 245665 | 1/2011 |
| IL | 238516 | 11/2013 |
| IL | 303851 | 6/2023 |
| JP | 53-139791 | 11/1978 |
| JP | 6-47058 | 2/1994 |
| JP | 10-290806 | 11/1998 |
| JP | 2001-037760 | 2/2001 |
| JP | 2001-556439 | 2/2001 |
| JP | 2003-341164 | 9/2003 |
| JP | 2009-269652 | 9/2003 |
| JP | 2012-246075 | 9/2003 |
| JP | 2005-169012 | 6/2005 |
| JP | 2011-529245 | 9/2009 |
| JP | 2015-010950 | 9/2009 |
| JP | 2016-201503 | 9/2009 |
| JP | 2012-548169 | 1/2011 |

(56) References Cited

FOREIGN PATENT DOCUMENTS

| | | |
|---|---|---|
| JP | 2013-1951 | 1/2011 |
| JP | 2015-540810 | 11/2013 |
| JP | 2017-156808 | 11/2013 |
| JP | 2018-088547 | 5/2018 |
| JP | 2018-232891 | 12/2018 |
| JP | 2021-026929 | 2/2021 |
| JP | 2023-537522 | 9/2023 |
| JP | 2023-555601 | 9/2023 |
| KR | 2003-0017897 | 3/2003 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO 2002/05699 | 1/2002 |
| WO | WO 2002/05897 | 1/2002 |
| WO | WO 2002/026319 | 4/2002 |
| WO | WO 2002/28302 | 4/2002 |
| WO | WO 2002/054941 | 7/2002 |
| WO | WO 2002/067797 | 9/2002 |
| WO | WO 2002/096304 | 12/2002 |
| WO | WO 2006/044794 | 4/2006 |
| WO | WO 2007/001981 | 1/2007 |
| WO | WO2007/008954 | 1/2007 |
| WO | WO 2007/031264 | 3/2007 |
| WO | WO 2008/001385 | 1/2008 |
| WO | WO 2008/008522 | 1/2008 |
| WO | WO 2008/076330 | 6/2008 |
| WO | WO 2008/076357 | 6/2008 |
| WO | WO 2008/121259 | 10/2008 |
| WO | WO 2008/140519 | 11/2008 |
| WO | WO 2008/141104 | 11/2008 |
| WO | WO2008/144709 | 11/2008 |
| WO | WO 2009/042172 | 4/2009 |
| WO | WO 2009/076461 | 6/2009 |
| WO | PCT/US2009/058329 | 9/2009 |
| WO | WO 2009/124192 | 10/2009 |
| WO | WO 2009/155319 | 12/2009 |
| WO | WO 2010/111246 | 9/2010 |
| WO | WO 2010/135606 | 11/2010 |
| WO | PCT/US2011/020535 | 1/2011 |
| WO | WO 2011/041038 | 4/2011 |
| WO | WO 2012/024162 | 2/2012 |
| WO | WO 2012/065753 | 3/2012 |
| WO | WO 2012/074932 | 6/2012 |
| WO | PCT/US2012/071465 | 12/2012 |
| WO | WO 2013/009516 | 1/2013 |
| WO | WO 2013/134452 | 9/2013 |
| WO | PCT/US2013/068012 | 11/2013 |
| WO | WO 2013/168006 | 11/2013 |
| WO | WO 2013/180947 | 12/2013 |
| WO | WO 2014/004051 | 1/2014 |
| WO | WO 2014/130231 | 8/2014 |
| WO | WO 2014/141207 | 9/2014 |
| WO | WO 2014/165194 | 10/2014 |
| WO | WO 2014/176141 | 10/2014 |
| WO | WO 2015/038317 | 3/2015 |
| WO | WO 2015/047817 | 4/2015 |
| WO | WO 2015/066295 | 5/2015 |
| WO | WO 2015/066303 | 5/2015 |
| WO | WO 2015/079319 | 6/2015 |
| WO | WO 2015/148105 | 10/2015 |
| WO | WO 2014/145222 | 1/2016 |
| WO | WO 2014/145659 | 1/2016 |
| WO | WO 2014/146029 | 1/2016 |
| WO | WO 2016/033380 | 3/2016 |
| WO | WO 2016/048965 | 3/2016 |
| WO | WO 2014/197596 | 4/2016 |
| WO | WO 2014/210373 | 5/2016 |
| WO | WO 2016/069157 | 5/2016 |
| WO | WO 2016/075544 | 5/2016 |
| WO | WO 2015/024013 | 6/2016 |
| WO | WO 2016/090420 | 6/2016 |
| WO | WO 2016/105448 | 6/2016 |
| WO | WO 2016/105449 | 6/2016 |
| WO | WO 2015/044945 | 8/2016 |
| WO | WO 2015/057696 | 8/2016 |
| WO | WO 2015/060927 | 8/2016 |
| WO | WO 2016/127130 | 8/2016 |
| WO | WO 2016/130686 | 8/2016 |
| WO | WO 2016/134273 | 8/2016 |
| WO | WO 2011/157714 | 9/2016 |
| WO | WO 2016/148954 | 9/2016 |
| WO | WO 2016/154091 | 9/2016 |
| WO | WO 2016/168381 | 10/2016 |
| WO | WO 2016/209682 | 12/2016 |
| WO | WO 2017/009472 | 1/2017 |
| WO | WO2017/010930 | 1/2017 |
| WO | WO 2017/019863 | 2/2017 |
| WO | WO 2017/027703 | 2/2017 |
| WO | WO 2017/027809 | 2/2017 |
| WO | WO 2018/116273 | 6/2018 |
| WO | PCT/US2020/050249 | 9/2020 |
| WO | WO 2020/198150 | 10/2020 |
| WO | WO 2021/016699 A1 | 2/2021 |
| WO | PCT/US2021/040843 | 7/2021 |
| WO | PCT/US2021/072125 | 10/2021 |
| WO | PCT/US2021/82125 | 10/2021 |
| WO | PCT/US2022/019954 | 3/2022 |
| WO | WO 2022/066743 A2 | 3/2022 |
| WO | WO 2022/125875 A1 | 6/2022 |
| WO | WO 2022/191978 A1 | 9/2022 |
| WO | WO 2022/207105 A1 | 10/2022 |
| WO | WO 2023/009697 A1 | 2/2023 |
| WO | PCT/US2023/017913 | 4/2023 |

OTHER PUBLICATIONS

U.S. Appl. No. 18/451,539, filed Aug. 17, 2023, Systems for Treating Nerves Within Bone.
U.S. Appl. No. 13/612,001 U.S. Pat. No. 8,419,731, filed Sep. 13, 2012, Methods of Treating Back Pain.
U.S. Appl. No. 16/153,242 U.S. Pat. No. 10,588,691, filed Oct. 5, 2018, Radiofrequencey Ablation of Tissue Within a Vertebral Body.
U.S. Appl. No. 16/160,155 U.S. Pat. No. 11,596,468, filed Oct. 15, 2018, Intraosseous Nerve Treatment.
U.S. Appl. No. 16/818,092 U.S. Pat. No. 11,737,814, filed Mar. 13, 2020, Radiofrequency Ablation of Tissue Within a Vertebral Body.
U.S. Appl. No. 17/394,189 U.S. Pat. No. 11,701,168, filed Aug. 4, 2021, Radiofrequency Ablation of Tissue Within a Vertebral Body.
U.S. Appl. No. 17/394,166 U.S. Pat. No. 11,690,667, filed Aug. 4, 2021, Radiofrequency Ablation of Tissue Within a Vertebral Body.
U.S. Appl. No. 18/360,724, filed Jul. 27, 2023, Radiofrequency Ablation of Tissue Within a Vertebral Body.
U.S. Appl. No. 17/193,491, filed Mar. 5, 2021, Method of Treating an Intraosseous Nerve
U.S. Appl. No. 13/963,767 U.S. Pat. No. 9,39,701, filed Aug. 9, 2013, Channeling Paths Into Bone.
U.S. Appl. No. 15/040,268 U.S. Pat. No. 10,265,099, filed Feb. 10, 2016, Systems for Accessing Nerves Within Bone.
U.S. Appl. No. 16/368,453, filed Mar. 28, 2019, Systems for Accessing Nerves Within Bone.
U.S. Appl. No. 16/205,050 U.S. Pat. No. 11,471,210, filed Nov. 29, 2018, Methods of Denervating Vertebral Body Using External Energy Source.
U.S. Appl. No. 18/047,164, filed Oct. 17, 2022, Methods of Denervating Vertebral Body Using External Energy Source.
U.S. Appl. No. 17/488,116 U.S. Pat. No. 11,234,764, filed Sep. 28, 2021, Systems for Navigation and Treatment Within a Vertebral Body.

(56) References Cited

OTHER PUBLICATIONS

U.S. Appl. No. 17/488,111 U.S. Pat. No. 11,291,502, filed Sep. 28, 2021, Methods of Navigation and Treatment Within a Vertebral Body.
U.S. Appl. No. 17/657,864, filed Apr. 4, 2022, Methods of Navigation and Treatment Within a Vertebral Body.
U.S. Appl. No. 17/138,203 U.S. Pat. No. 11,123,103, filed Dec. 30, 2020, Introducer Systems for Bone Access.
U.S. Appl. No. 17/138,234 U.S. Pat. No. 11,007,010, filed Dec. 30, 2020, Curved Bone Access Systems.
U.S. Appl. No. 17/302,949 U.S. Pat. No. 11,202,655, filed Mar. 17, 2021, Accessubg and Treating Tissue Within a Vertical Body.
U.S. Appl. No. 17/303,254 U.S. Pat. No. 11,426,199, filed May 25, 2021, Methods of Treating a Vertebral Body.
U.S. Appl. No. 17/303,267 U.S. Pat. No. 11,207,100, filed May 25, 2021, Methods of Detecting and Treating Back Pain.
U.S. Appl. No. 17/645,658, filed Dec. 22, 2021, Methods of Detecting and Treating Back Pain.
U.S. Appl. No. 17/822,700, filed Aug. 26, 2022, Methods of Treating a Vertebral Body.
U.S. Appl. No. 18/003,760, filed Dec. 29, 2022, Vertebral Denervation in Conjunction With Vertebral Fusion.
U.S. Appl. No. 18/258,734, filed Jun. 21, 2023, Prediction of Candicates for Spinal Neuromodulation.
U.S. Appl. No. 18/339,007, filed Jun. 21, 2023, Prediction of Candicates for Spinal Neuromodulation.
U.S. Appl. No. 18/550,040, filed Sep. 11, 2023, Robotic Spine Systems and Robotic-Assisted Methods for Tissue Modulation.
U.S. Appl. No. 18/053,284, filed Nov. 7, 2022, Impedance Stoppage Mitigation During Radiofrequency Tissue Ablation Procedures.
A Novel Approach for Treating Chronic Lower Back Pain Abstract for Presentation at North American Spine Society 26th Annual Meeting in Chicago IL on Nov. 4, 2011.
Antonacci M. Darryl et al.; Innervation of the Human Vertebral Body: A Histologic Study; Journal of Spinal Disorder vol. 11 No. 6 pp. 526-531 1998 Lippincott Williams & Wilkins Philadelphia.
Arnoldi Carl C.; Intraosseous Hypertension—A Possible Cause of Low Back Pain ?; Clinical Orthopedics and Related Research No. 115 Mar.-Apr. 1976.
Bailey, Jeannie F., "Innervation Patterns of PGP 9.5-Positive Nerve Fibers within the Human Lumbar Vertebra," Journal of Anatomy, (2011) 218, pp. 263-270, San Francisco, California.
Becker, Stephan, et al., "Ablation of the basivertebral nerve for treatment of back pain: a clinical study," The Spine Journal, vol. 17, pp. 218-223 (Feb. 2017).
Bergeron et al. "Fluoroscopic-guided radiofrequency ablation of the basivertebral nerve: application and analysis with multiple imaging modalities in an ovine model" Thermal Treatment of Tissue: Energy Delivery and Assessment III edited by Thomas p. Ryan Proceedings of SPIE vol. 5698 (SPIE Bellingham WA 2005) pp. 156-167.
Bogduk N. The anatomy of the lumbar intervertebral disc syndrome Med J. Aust. 1976 Vol. 1 No. 23 pp. 878-881.
Bogduk Nikolai et al.; Technical Limitations to the efficacy of Radiofrequency Neurotomy for Spinal Pain; Neurosurgery vol. 20 No. 4 1987.
Caragee, EG et al.; "Discographic, MRI and psychosocial determinants of low back pain disability and remission: A prospective study in subjects with benign persistent back pain", The Spine Journal: The Official Journal of the North American Spine Society, vol. 5(1), pp. 24-35 (2005).
Choy Daniel SS.J et al.; Percutaneous Laser Disc Decompression A New Therapeutic Modality; SPINE vol. 17 No. 8 1992.
Cosman E.R. et al. Theoretical Aspects of Radiofrequency Lesions in the Dorsal Root Entry Zone. Neurosurgery vol. 1 no. 6 1984 pp. 945-950.
Deardorff Dana L. et al.; Ultrasound applicators with internal cooling for interstitial thermal therapy; SPIE vol. 3594 1999.
Deramond H. et al. Temperature Elevation Caused by Bone Cement Polymerization During Vertebroplasty Bone Aug. 1999 p. 17S-21S vol. 25 No. 2 Supplement.
Diederich C. J. et al. "IDTT Therapy in Cadaveric Lumbar Spine: Temperature and thermal dosedistributions Thermal Treatment of Tissue: Energy Delivery and Assessment" Thomas P. Ryan Editor Proceedings of SPIE vol. 4247:104-108 (2001).
Diederich Chris J. et al.; Ultrasound Catheters for Circumferential Cardiac Ablation; SPIE vol. 3594 (1999).
Dupuy D.E. et al. Radiofrequency ablation of spinal tumors: Temperature distribution in the spinal canal AJR vol. 175 pp. 1263-1266 Nov. 2000.
Dupuy Damian E.; Radiofrequency Ablation: An Outpatient Percutaneous Treatment; Medicine and Health/Rhode Island vol. 82 No. 6 Jun. 1999.
Esses Stephen I. et al.; Intraosseous Vertebral Body Pressures; SPINE vol. 17 No. 6 Supplement 1992.
FDA Response to 510(k) Submission by Relievant Medsystems Inc. submitted on Sep. 27, 2007 (date stamped on Oct. 5, 2007) and associated documents.
Fields, AJ et al; "Innervation of pathologies in the lumbar vertebral endplate and intervertebral disc", The Spine Journal: Official Journal of the North American Spine Society, vol. 14(3), pp. 513-521 (2014).
Fields, Aaron J. et al.; "Cartilage endplate damage strongly assocates with chronic low back pain, independent of modic changes", Abstract form Oral Presentation at the ISSLS Annual Meeting in Banff, Canada (May 14-18, 2018).
Fischgrund JS, et al.; "Intraosseous Basivertebral Nerve Ablation for the Treatment of Chronic LowBack Pain: 2-Year Results from a Prospective Randomized Double-Blind Sham-Controlled Multicenter Study", International Journal of Spine Surgery, vol. 13 (2), pp. 110-119 (2019).
Fras M.D., Christian et al., "Substance P-containing Nerves within the Human Vertebral Body: An Immunohistochemical Study of the Basivertebral Nerve", The Spine Journal 3, 2003, pp. 63-67.
Gehl J. "Electroporation: theory and methods perspectives for drug delivery gene therapy and research" Acta Physiol. Scand. Vol. 177 pp. 437-447 (2003).
Goldberg S.N. et al. Tissue ablation with radiofrequency: Effect of probe size gauge duration and temperature on lesion volume Acad. Radiol. vol. 2 pp. 399-404 (1995).
Gornet, Matthew G et al.; "Magnetic resonance spectroscopy (MRS) can identify painful lumbar discsand may facilitate improved clinical outcomes of lumbar surgeries for discogenic pain", European Spine Journal, vol. 28, pp. 674-687 (2019).
Hanai Kenji et al.; Simultaneous Measurement of Intraosseous and Cerebrospinal Fluid Pressures in the Lumbar Region; SPINE vol. 10 No. 1 1985.
Heggeness Michael H. et al. The Trabecular Anatomy of Thoracolumbar Vertebrae: Implications for Burst Fractures Journal of Anatomy 1997 pp. 309-312 vol. 191 Great Britain.
Heggeness Michael H. et al. Discography Causes End Plate Deflection; SPINE vol. 18 No. 8 pp. 1050-1053 1993 J.B. Lippincott Company.
Heggeness, M. et al Ablation of the Basivertebral Nerve for the Treatment of Back Pain: A PilotClinical Study; The Spine Journal, 2011, vol. 11, Issue 10, Supplement, pp. S65-S66, ISSN 1529-9430.
Hoopes et al. "Radiofrequency Ablation of The Basivertebral Nerve as a Potential Treatment of Back Pain: Pathologic Assessment in an Ovine Model" Thermal Treatment of Tissue: Energy Delivery and Assessment III edited by Thomas P. Ryan Proceedings of SPIE vol. 5698 (SPIE Bellingham WA 2005) pp. 168-180.
Houpt Jonathan C. et al.; Experimental Study of Temperature Distributions and Thermal TransportDuring Radiofrequency Current Therapy of the Intervertebral Disc; SPINE vol. 21 No. 15 pp. 1808-1813 1996 Lippincott-Raven Publishers.
Jourabchi, Natanel et al.; "Irreversible electroporation (NanoKnife) in cancer treatment," Gastrointestinal Intervention, vol. 3, pp. 8-18 (2014).
Khalil, J et al.; "A Prospective, Randomized, Multi-Center Study of Intraosseous Basivertebral Nerve Ablation for the Treatment of Chronic Low Back Pain", The Spine Journal (2019), avilable at https://doi.org/10.1016/jspinee.2019.05.598.

(56) References Cited

OTHER PUBLICATIONS

Kleinstueck Frank S. et al.; Acute Biomechanical and Histological Effects of Intradiscal Electrothermal Therapy on Human Lumbar Discs; SPINE vol. 26 No. 20 pp. 2198-2207; 2001 Lippincott Williams & Wilkins Inc.

Kopecky Kenyon K. et al. "Side-Exiting Coaxial Needle for Aspiration Biopsy"—AJR—1996; 167 pp. 661-662.

Kuisma M et al.; "Modic changes in endplates of lumbar vertebral bodies: Prevalence and associationwith low back and sciatic pain among middle-aged male workers", Spine, vol. 32(10), pp. 1116-1122 (2007).

Lehmann Justus F. et al.; Selective Heating Effects of Ultrasound in Human Beings; Archives of Physical Medicine & Rehabilitation Jun. 1966.

Letcher Frank S. et al.; The Effect of Radiofrequency Current and Heat on Peripheral Nerve Action Potential in the Cat; U.S. Naval Hospital Philadelphia PA. (1968).

Lotz JC, et al.; "The Role of the Vertebral End Plate in Low Back Pain", Global Spine Journal, vol. 3, pp. 153-164 (2013).

Lundskog Jan; Heat and Bone Tissue-/an experimental investigation of the thermal properties of bone tissue and threshold levels for thermal injury; Scandinavian Journal of Plastic and Reconstructive Surgery Supplemental 9 From the Laboratory of Experimental Biology Department of anatomy University of Gothenburg Gothenburg Sweden GOTEBORG 1972.

Martin J.B. et al. Vertebroplasty: Clinical Experience and Follow-up Results Bone Aug. 1999 pp. 11S-15S vol. 25 No. 2 Supplement.

Massad Malek M.D. et al.; Endoscopic Thoracic Sympathectomy: Evaluation of Pulsatile Laser Non-Pulsatile Laser and Radiofrequency-Generated Thermocoagulation; Lasers in Surgery and Medicine; 1991; pp. 18-25.

Mehta Mark et al.; The treatment of chronic back pain; Anaesthesia 1979 vol. 34 pp. 768-775.

Modic MT et al.; "Degenerative disk disease: assessment of changes in vertebral body marrow with MR imaging" Radiology vol. 166 pp. 193-199 (1988).

Mok, Florence et al.; "Modic changes of the lumbar spine: Prevalence, risk factors, and association with disc degeneration and low back pain in a large-scale population-based cohort", The Spine Journal: Official Journal of the North American Spine Society, vol. 16(1), pp. 32-41 (2016).

Nau William H. Ultrasound interstitial thermal therapy (USITT) in the prostate; SPIE vol. 3594 Jan. 1999.

Osteocool Pain Management Brochure, Baylis Medical, copyright 2011.

Pang, Henry et al,; The UTE Disc Sign on MRI: A Novel Imaging Biomarker Associated With Degenerative Spine Changes, Low Back Pain, and Disability, SPINE, vol. 42 (Aug. 2017).

Radiological Society of North America. "Pulsed radiofrequency relieves acute back pain and sciatica."ScienceDaily. ScienceDaily, Nov. 27, 2018. <www.sciencedaily.com/releases/2018/11/181127092604.htm>.

Rashbaum Ralph F.; Radiofrequency Facet Denervation A Treatment alternative in Refractory Low Back Pain with or without Leg Pain; Orthopedic Clinics of North America-vol. 14 No. 3 Jul. 1983.

Rosenthal D.I. Seminars in Musculoskeletal Radiology vol. 1 No. 2. pp. 265-272 (1997).

Ryan et al. "Three-Dimensional Finite Element Simulations of Vertebral Body Thermal Treatment"Thermal Treatment of Tissue: Energy Delivery and Assessment III edited by Thomas P. Ryan Proceedings of SPIE vol. 5698 (SPIE Bellingham WA 2005) pp. 137-155.

Shealy C. Norman; Percutaneous radiofrequency denervation of spinal facets Treatment for chronic back pain and sciatica; Journal of Neurosurgery/vol. 43/Oct. 1975.

Sherman Mary S.; The Nerves of Bone The Journal of Bone and Joint Surgery Apr. 1963 pp. 522-528 vol. 45-A No. 3.

Solbiati L. et al. Hepatic metastases: Percutaneous radio-frequency ablation with cooled-tip electrodes. Interventional Radiology vol. 205 No. 2 pp. 367-373 (1997).

Stanton Terry "Can Nerve Ablation Reduce Chronic Back Pain ?" AAOS Now Jan. 2012.

The AVAmax System—Cardinal Health Special Procedures Lit. No. 25P0459-01—www.cardinal.com (copyright 2007).

Tillotson L. et al. Controlled thermal injury of bone: Report of a percutaneous technique using radiofrequency electrode and generator. Investigative Radiology Nov. 1989 pp. 888-892.

Troussier B. et al.; Percutaneous Intradiscal Radio-Frequency Thermocoagulation A Cadaveric Study; SPINE vol. 20 No. 15 pp. 1713-1718 1995 Lippincott-Raven Publishers.

Ullrich Jr. Peter F. "Lumbar Spinal Fusion Surgery" Jan. 9, 2013 Spine-Health (available via wayback machine Internet archive at http://web.archive.org/web/20130109095419/http://www/spine-health.com/treatment/spinal-fusion/lumbar-spinal-fusion-surgery).

Weishaupt, D et al,; "Painful Lumbar Disk Derangement: Relevance of Endplate Abnormalities at MR Imaging", Radiology, vol. 218(2), pp. 420-427 (2001).

YouTube Video, "DFINE-STAR Procedure Animation," dated Sep. 30, 2013, can be viewed at https://www.youtube.com/watch?v=YxtKNyc2e-0.

Kim et al., Transforaminal epiduroscopic basivertebral nerve laser ablation for chronic low back painassociated with modic changes: A preliminary open-label study. Pain Research and Management 2018; https://pubmed.ncbi.nlm.nih.gov/30186540.

Rahme et al., The modic vertebral endplate and marrow changes: pathologic significance and relationto low back pain and segmental instability of the lumbar spine. American Journal of Neuroradiology 29.5 (2008): 838-842; http://www.ajnr.org/content/29/5/838.

Macadaeg et al, A prospective single arm study of intraosseous basivertebral nerve ablation for the treatment of chronic low back pain: 12-month results. North American Spine Society Journal; May 27, 2020, 8 pages.

Vadala et al., "Robotic Spine Surgery and Augmented Reality Systems: A State of the Art", Neurospine Epub Mar. 31, 2020; received: Feb. 2, 2020; revised: Feb. 22, 2020; accepted: Feb. 24, 2020; retrieved on [Oct. 6, 2022]. Retrieved from the internet URL:https://www.ncbi.nlm.nih.gov/pmc/articles/PMC7136092/pdf/ns-2040060-030.pdf entire document.

U.S. Appl. No. 09/775,137 U.S. Pat. No. 6,699,242, filed Feb. 1, 2001, Methods and Devices for Intraosseous Nerve Ablation.

U.S. Appl. No. 10/401,854 U.S. Pat. No. 7,258,690, filed Mar. 28, 2003, Windowed Thermal Ablation Probe.

U.S. Appl. No. 11/745,446, filed May 7, 2007, Windowed Thermal Ablation Probe.

U.S. Appl. No. 12/643,997, filed Dec. 21, 2009, Windowed Thermal Ablation Probe.

U.S. Appl. No. 13/655,683 U.S. Pat. No. 8,882,764, filed Oct. 19, 2012, Thermal Denervation Devices.

U.S. Appl. No. 14/535,868 U.S. Pat. No. 9,848,944, filed Nov. 7, 2014, Thermal Denervation Devices and Methods.

U.S. Appl. No. 15/845,699, filed Dec. 18, 2017, Thermal Denervation Devices and Methods.

U.S. Appl. No. 16/153,407 U.S. Pat. No. 10,463,423, filed Oct. 5, 2018, Thermal Denervation Devices and Methods.

U.S. Appl. No. 10/260,879 U.S. Pat. No. 6,907,884, filed Sep. 30, 2002, Method of Straddling an Intraosseous Nerve.

U.S. Appl. No. 11/123,766 U.S. Pat. No. 7,749,218, filed May 6, 2005, Method of Straddling an Intraosseous Nerve.

U.S. Appl. No. 12/683,555 U.S. Pat. No. 8,613,744, filed Jan. 7, 2010, Systems and Methods for Navigating an Instrument Through Bone.

U.S. Appl. No. 13/612,561 U.S. Pat. No. 8,425,507, filed Sep. 12, 2012, Basivertebral Nerve Denervation.

U.S. Appl. No. 13/617,470 U.S. Pat. No. 8,623,014, filed Sep. 14, 2012, Systems for Denervation of Basivertebral Nerves.

U.S. Appl. No. 13/862,306 U.S. Pat. No. 8,628,528, filed Apr. 12, 2013, Vertebral Denervation.

U.S. Appl. No. 14/136,763 U.S. Pat. No. 9,023,038, filed Dec. 20, 2013, Denervation Methods.

U.S. Appl. No. 14/174,024 U.S. Pat. No. 9,017,325, filed Jan. 3, 2014, Nerve Modulation Systems.

U.S. Appl. No. 14/174,024 U.S. Pat. No. 9,017,325, files Jan. 3, 2014, Nerve Modulation Systems.

(56) References Cited

OTHER PUBLICATIONS

U.S. Appl. No. 14/153,922 U.S. Pat. No. 9,173,676, filed Jan. 13, 2014, Nerve Modulation Systems.
U.S. Appl. No. 14/695,330 U.S. Pat. No. 9,421,064, filed Apr. 24, 2015, Nerve Modulation Systems.
U.S. Appl. No. 14/701,908, filed May 1, 2015, Denervation Methods.
U.S. Appl. No. 14/928,037 U.S. Pat. No. 10,028,753, filed Oct. 30, 2015, Spine Treatment Kits.
U.S. Appl. No. 15/241,523 U.S. Pat. No. 9,724,107, filed Aug. 19, 2016, Nerve Modulation Systems.
U.S. Appl. No. 15/669,399 U.S. Pat. No. 10,905,440, filed Aug. 4, 2017, Nerve Modulation Systems.
U.S. Appl. No. 16/152,834, filed Oct. 5, 2018, Bipolar Radiofrequency Ablation Systems for Treatment Within Bone.
U.S. Appl. No. 16/156,850, filed Oct. 10, 2018, Systems for Treating Nerves Within Bone Using Steam.
U.S. Appl. No. 16/747,830, filed Jan. 21, 2020, Denervation Methods.
U.S. Appl. No. 13/612,541 U.S. Pat. No. 8,361,067 filed Sep. 12, 2012, Methods of Therapeutically Heating a Vertebral Body to Treat Back Pain.
U.S. Appl. No. 13/615,001 U.S. Pat. No. 8,419,731, filed Sep. 13, 2012, Methods of Treating Back Pain.
U.S. Appl. No. 13/615,300, filed Sep. 13, 2012, System for Heating a Vertebral Body to Treat Back Pain.
U.S. Appl. No. 13/862,317 U.S. Pat. No. 8,992,522, filed Apr. 12, 2013, Back Pain Treatment Methods.
U.S. Appl. No. 13/923,798 U.S. Pat. No. 8,992,523, filed Jun. 12, 2013, Vertebral Treatment.
U.S. Appl. No. 14/673,172 U.S. Pat. No. 9,486,279, filed Mar. 30, 2015, Intraosseous Nerve Treatment.
U.S. Appl. No. 15/344,284 U.S. Pat. No. 10,111,704, filed Nov. 4, 2016, Intraosseous Nerve Treatment.
U.S. Appl. No. 16/153,234 U.S. Pat. No. 10,478,246, filed Oct. 5, 2018, Ablation of Tissue Within Vertebral Body Involving Internal Cooling.
U.S. Appl. No. 16/153,242 U.S. Pat. No. 10,588,691, filed Oct. 5, 2018, Radiofrequency Ablation of Tissue Within a Vertebral Body.
U.S. Appl. No. 16/160,155, filed Oct. 15, 2018, Intraosseous Nerve Treatment.
U.S. Appl. No. 16/818,092, filed Mar. 2020, Radiofrequency Ablation of Tissue Within a Vertebral Body.
U.S. Appl. No. 17/394,189, filed Aug. 4, 2021, Radiofrequency Ablation of Tissue Within a Vertebral Body.
U.S. Appl. No. 17/394,166, filed Aug. 4, 2021, Radiofrequency Ablation of Tissue Within a Vertebral Body.
U.S. Appl. No. 13/541,591 U.S. Pat. No. 7,749,218 RE46356, filed Jul. 3, 2012, Method of Treating an Intraosseous Nerve.
U.S. Appl. No. 15/469,315 U.S. Pat. No. 7,749,218 RE48460, filed Mar. 24, 2017, Method of Treating an Intraosseous Nerve.
U.S. Appl. No. 16/153,598, filed Oct. 5, 2018, Method of Treating an Intraosseous Nerve.
U.S. Appl. No. 16/153,603, filed Oct. 5, 2018, Method of Treating an Intraosseous Nerve.
U.S. Appl. No. 12/566,895 U.S. Pat. No. 8,419,730, filed Sep. 25, 2009, Systems and Methods for Navigating an Instrument Through Bone.
U.S. Appl. No. 13/963,767 U.S. Pat. No. 9,039,701, filed Aug. 9, 2013, Channeling Paths Into Bone.
U.S. Appl. No. 13/862,242 U.S. Pat. No. 9,259,241, filed Apr. 12, 2013, Systems for Accessing Nerves Within Bone.
U.S. Appl. No. 15/040,268 U.S. Pat. No. 10,265,099, filed Feb. 10, 2016, Systems for Accessing Nerves Within Bones.
U.S. Appl. No. 16/368,453, filed Mar. 28, 2019, Systems for Accessing Nerves Within Bones.
U.S. Appl. No. 12/868,818 U.S. Pat. No. 8,808,284, filed Aug. 26, 2010, Systems for Navigating an Instrument Through Bone.
U.S. Appl. No. 14/462,371 U.S. Pat. No. 9,265,522, filed Aug. 18, 2014, Methods for Navigating an Instrument Through Bone.
U.S. Appl. No. 13/543,712 U.S. Pat. No. 8,535,309, filed Jul. 6, 2012, Vertebral Bone Channeling Systems.
U.S. Appl. No. 13/543,723 U.S. Pat. No. 8,414,571, filed Jul. 6, 2012, Vertebral Bone Navigation Systems.
U.S. Appl. No. 13/543,721, filed Jul. 6, 2012, Intraosseous Nerve Denervation Methods.
U.S. Appl. No. 10/103,439 U.S. Pat. No. 6,736,835, filed Mar. 21, 2002, Novel Early Intervention Spinal Treatment Methods and Devices for Use Therein.
U.S. Appl. No. 14/369,661 U.S. Pat. No. 10,369,661, filed Jun. 27, 2014, Systems and Methods for Treating Back Pain.
U.S. Appl. No. 16/205,050, filed Nov. 29, 2018, Methods of Denervating Vertebral Body Using External Energy Source.
U.S. Appl. No. 14/440,050 U.S. Pat. No. 9,775,627, filed Apr. 30, 2015, Systems and Methods for Creating Curved Paths Through Bone and Modulating Nerves With The Bone.
U.S. Appl. No. 15/722,392 U.S. Pat. No. 10/357,258, filed Oct. 2, 2017, Systems and Methods for Creating Curved Paths Through Bone and Modulating Nerves With The Bone.
U.S. Appl. No. 16/370,264 U.S. Pat. No. 10/517,611, filed Mar. 29, 2019, Systems for Navigation and Treatment Within a Vertebral Body.
U.S. Appl. No. 16/717,985 U.S. Pat. No. 11/160,563, filed Dec. 17, 2019, Systems for Navigation and Treatment Within a Vertebral Body.
U.S. Appl. No. 17/488,116, filed Sep. 28, 2021, Systems for Navigation and Treatment Within a Vertebral Body.
U.S. Appl. No. 17/488,111, filed Sep. 28, 2021, Methods of Navigation and Treatment Within a Vertebral Body.
U.S. Appl. No. 14/454,643 U.S. Pat. No. 9,724,151, filed Aug. 7, 2014, Modulating Nerves Within Bone Using Bone Fasteners.
U.S. Appl. No. 15/669,292 U.S. Pat. No. 10/456,187, filed Aug. 4, 2017, Modulating Nerves Within Bone Using Bone Fasteners.
U.S. Appl. No. 16/661,271 U.S. Pat. No. 11,065,046, filed Oct. 23, 2019, Modulating Nerves Within Bone Using Bone Fasteners.
U.S. Appl. No. 17/378,457, filed Jul. 16, 2021, Modulating Nerves Within Bone.
U.S. Appl. No. 17/138,203, filed Dec. 30, 2020, Introducer Systems for Bone Access.
U.S. Appl. No. 17/302,949, filed Mar. 17, 2021, Accessing and Treating Tissue Within a Vertical Body.
U.S. Appl. No. 17/303,254, filed Mar. 25, 2021, Methods of Treating a Vertebral Body.
U.S. Appl. No. 17/303,267, filed Mar. 25, 2021, Methods of Detecting and Treating Back Pain.

\* cited by examiner

INTRODUCER DRILL

RELATED APPLICATIONS

This application claims priority to U.S. Provisional Application No. 63/084,381 filed Sep. 28, 2020, the entire content of which is hereby incorporated by reference herein.

FIELD

Described herein are various implementations of systems, devices and methods for accessing bone (e.g., vertebral bodies of the spine) using a curveable, or steerable, introducer drill to facilitate access to target treatment locations within bone along a curved trajectory, especially in "hard" bone, or bone having a high or normal (e.g., non-osteoporotic or non-osteopenic) bone mass density.

BACKGROUND

Back pain is a very common health problem worldwide and is a major cause for work-related disability benefits and compensation. At any given time, low back pain impacts nearly 30% of the US population, leading to 62 million annual visits to hospitals, emergency departments, outpatient clinics, and physician offices. Back pain may arise from strained muscles, ligaments, or tendons in the back and/or structural problems with bones or spinal discs. The back pain may be acute or chronic. Existing treatments for chronic back pain vary widely and include physical therapy and exercise, chiropractic treatments, injections, rest, pharmacological therapy such as opioids, pain relievers or anti-inflammatory medications, and surgical intervention such as vertebral fusion, discectomy (e.g., total disc replacement), or disc repair. Existing treatments can be costly, addictive, temporary, ineffective, and/or can increase the pain or require long recovery times. In addition, existing treatments do not provide adequate relief for the majority of patients and only a small percentage are surgically eligible.

SUMMARY

Applicant's existing technology (the Intracept® procedure by Relievant®) offers a safe and effective minimally invasive procedure that targets the basivertebral nerve for the relief of chronic vertebrogenic low back pain. As disclosed herein, several embodiments provide adjunct technologies to facilitate access to target treatment locations within bone (e.g., within one or more vertebral bodies of a spine of a human or veterinary subject) that are only accessible (or that are more feasibly accessible) using a curved trajectory, especially target treatment locations in "hard" bone, or bone having a high or normal (e.g., non-osteoporotic or non-osteopenic) bone mass density.

Several implementations described herein are directed to systems and methods for accessing target treatment or diagnostic locations within bone (e.g., a vertebral body). In some embodiments, an intraosseous nerve (e.g., basivertebral nerve) within a bone (e.g., vertebral body) of the spine is accessed using a steerable, or curveable, introducer drill so as to facilitate treatment, or prevention of, back pain (e.g., chronic low back pain, acute back pain, or other ailments or conditions associated with the spine (e.g., vertebral fractures, spinal tumors, scoliosis, spondylosis)). The introducer drill may advantageously form a passageway within bone to facilitate insertion of additional instruments to the target treatment location or diagnostic location within bone. However, the introducer drill may also advantageously function as both an access and treatment instrument in some embodiments. In some embodiments, the introducer drill may advantageously facilitate access to locations within bone (e.g., posterior portions of a vertebral body) that may be difficult to access using straight instruments alone or using pre-curved instruments.

In accordance with several embodiments, a kit or system of access tools (and optionally one or more treatment or diagnostic instruments) may include a steerable, or curveable, introducer drill. The steerable, or curveable, introducer drill may advantageously facilitate access to a target treatment location of a terminus of a basivertebral nerve located in a posterior half of the vertebral body and within a region approximately 0%-50% (e.g., 5%-15%, 5%-25%, 10%-30%, 10%-40%, 20%-50%, 10%-35%, 20%-40%, overlapping ranges thereof, or any value within the recited ranges) of the distance between posterior and anterior walls of the vertebral body and approximately aligned with a sagittal plane or a central spinous process of the vertebral body). The steerable, or curveable, introducer drill may access the target treatment location along a curved trajectory after using a transpedicular (i.e., through a pedicle) access approach. However, other approaches (e.g., anterior, lateral, posterior lateral, anterior lateral, non-transpedicular) are possible. The kit or system may include a radiofrequency energy delivery device (e.g., a bipolar radiofrequency energy delivery probe configured to be operatively coupled to a radiofrequency generator or a battery-operated radiofrequency energy delivery device).

The steerable, or curveable, introducer drill may advantageously be used in hard bone. Hard bone may be determined based on bone mass density testing, compressive strength determinations, compressive modulus determinations, imaging modalities, or based on tactile feel by the operator as access instruments are being advanced. In some implementations, hard bone may be determined as bone having a bone mineral density score within a standard deviation of a normal healthy young adult (e.g., a T score greater than or equal to −1). In some implementations, hard bone may be identified as bone having a compressive strength of greater than 4 MPa and/or a compressive modulus of greater than 80 MPa for cancellous bone and greater than 5.5 MPa and/or a compressive modulus of greater than 170 MPa for cortical bone.

In accordance with several embodiments, a curveable introducer drill configured to access a target treatment region within hard bone along a curved trajectory includes a drive shaft comprising a proximal rotational member (e.g., paddle, handle, knob, crank), a distal drill tip, and an elongate shaft portion extending from the proximal rotational member to the distal drill tip. The distal drill tip is sharp and includes cutting flutes (e.g., top and/or side cutting flutes). The curveable introducer drill further includes an outer tube surrounding the drive shaft. A distal end portion of the outer tube includes a segmented tube section configured to facilitate controlled bending of the segmented tube section of the outer tube. The introducer drill also includes an actuator operably coupled to the drive shaft and adapted to apply tension to the drive shaft which, in turn, causes the segmented tube section of the outer tube, and thus the entire distal end portion of the introducer drill, to bend.

The outer tube may comprise a shape memory material (e.g., nitinol or other metallic alloy or a shape-memory polymer) that is shape set to have a straight configuration when unconstrained. The outer tube may include a proximal housing at its proximal end and the proximal rotational member may extend out of a proximal end of the proximal housing of the outer tube. In some embodiments, one side (e.g., one and only one side) of a distal end portion of the outer tube comprises a segmented tube section or zone comprised of tube segments and slits, gaps, apertures, or slots configured to facilitate controlled bending of the segmented tube section of the outer tube in a single known direction (as opposed to uncontrolled bending in any direction). The slits, gaps, apertures, or slots may be formed by laser cutting, for example. In some implementations, the drive shaft (upon application of tension by the actuator) exerts a lateral force on the segmented tube section of the outer tube to cause the controlled bending of the segmented tube section in the single known direction. In some embodiments, the drive shaft can generate a lateral force of between 0.25 pounds and 10 pounds (between 0.25 pounds and 1.5 pounds, between 0.5 pounds and 2.5 pounds, between 1 pound and 5 pounds, between 2 pounds and 8 pounds, between 4 pounds and 10 pounds, overlapping ranges thereof, or any value within the recited ranges, such as 0.25 pounds, 0.5 pounds, 1 pound, 1.5 pounds, 2 pounds, 2.5 pounds, 3 pounds, 3.5 pounds, 4 pounds, 4.5 pounds, 5 pounds, 5.5 pounds, 6 pounds, 6.5 pounds, 7 pounds, 7.5 pounds, 8 pounds, 8.5 pounds, 9 pounds, 9.5 pounds, 10 pounds, or more) by activating the actuator.

The proximal housing of the outer tube may include an indicator (e.g., arrow, line, dot, or other visual indicia or marking) configured to indicate the single known direction of bending or curving. The introducer drill may further include a compression spring mechanically coupled to a proximal end of the outer tube. The introducer drill may also include a bushing and/or thrust bearing and/or roller bearing positioned between a distal edge of the outer tube and a proximal edge of the distal drill tip.

The actuator may include a lever. In such implementations, the lever may be operably coupled to the drive shaft (e.g., via a cam assembly) and be adapted to apply tension to the drive shaft which, in turn, exerts a lateral force on the segmented tube section of the outer tube to cause the controlled bending of the segmented tube section in the single known direction. The actuator may alternatively not include a lever actuator and may instead comprise a pull wire assembly, a slider, or a rotational member, such as a wheel, crank, or knob. The actuator may be actuated by a single finger (e.g., thumb, index, or middle finger) or multiple fingers working together. In several embodiments, the introducer drill may be adapted for single-hand operation (e.g., advancement and actuation using a single hand).

The outer tube may comprise a conductive portion configured or adapted to form a proximal electrode of a bipolar electrode pair with the drill tip functioning as a distal electrode of the bipolar electrode pair when radiofrequency energy is applied to the drill tip via one or more electrically conductive wires or leads coupled between the drill tip and a radiofrequency generator. At least a portion of the outer tube may comprise a conformal, anodized coating. The coating may not be electrically conductive (e.g., may provide an insulation function). The introducer drill may be configured to be advanced through a previously-introduced introducer cannula. The introducer cannula may have a distal opening at its tip. The distal opening may be an axial opening or a radial side window.

In some implementations, the introducer drill may include an inner tube coupled (e.g., attached, welded, bonded) to the distal end of the drive shaft and the inner tube may be configured to apply compressive force to cause lateral bending of the segmented tube section of the outer tube instead of the drive shaft, thereby allowing the drive shaft to be focused on controlling the distal drill tip and the drilling function. The inner tube may be comprised of shape memory material (e.g., nitinol or other metallic alloy).

In accordance with several embodiments, a method of accessing a target treatment location within a vertebral body includes inserting at least a distal drill tip of a steerable, or curveable, introducer drill along a straight path through at least a portion of a pedicle of the vertebral body. The introducer drill may include a drive shaft including a proximal rotational member, the distal drill tip, and an elongate shaft portion extending from the proximal rotational member to the distal drill tip. The introducer drill may also include an outer tube surrounding the drive shaft, the outer tube comprising a proximal housing, with the proximal rotational member extending out of a proximal end of the proximal housing of the outer tube. In some embodiments, one (e.g., one and only one) side of a distal end portion of the outer tube comprises a segmented tube section comprised of tube segments and slits configured to facilitate controlled bending of the segmented tube section of the outer tube in a single known direction. The introducer also includes an actuator operably coupled to the drive shaft and adapted to apply tension to the drive shaft which, in turn, causes the segmented tube section of the outer tube to bend in the single known direction. The method further includes advancing the introducer drill within the vertebral body while actuating the actuator so as to facilitate advancement of the distal drill tip along a curved trajectory toward a target treatment region within a posterior half of the vertebral body.

In some embodiments, inserting at least the distal drill tip of the curveable introducer drill along the straight path through at least the portion of the pedicle of the vertebral body comprises inserting the curveable introducer drill through a straight introducer cannula that was previously inserted. The method (or steps thereof) may be performed under fluoroscopy or other imaging modality. The further advancing step may include adjusting a radius of curvature using the actuator as the introducer drill is advanced. The method may further include applying radiofrequency energy to the target treatment region using the curveable introducer drill, wherein the distal drill tip is configured to act as a distal electrode of a bipolar electrode pair and a conductive portion of the outer tube is configured to act as a proximal electrode of the bipolar electrode pair. In some embodiments, the applied radiofrequency energy is sufficient to modulate (e.g., ablate, denervate) an intraosseous nerve (e.g., basivertebral nerve) within the vertebral body. In some embodiments, the radiofrequency energy is applied by a separate radiofrequency energy delivery probe (e.g., bipolar radiofrequency energy delivery device operatively coupled to a radiofrequency generator) that is inserted (e.g., through an introducer cannula) within the vertebral body along a path formed by the introducer drill after removal of the introducer drill.

The method may optionally include sensing or detecting the presence of nerves during insertion of the introducer drill via one or more sensors located along the introducer drill. For example, nerves within or adjacent a pedicle may be sensed upon insertion of the drill through a pedicle or through bone via another insertion approach. A basivertebral nerve location may be sensed or detected upon advancement of the drill within the cancellous bone portion of the vertebral body. The method may include determining whether ablation of a nerve within the bone (e.g., basivertebral nerve within a vertebral body) has been successful (e.g., through stimulation and monitoring via the one or more sensors, which may include one or more stimulation and/or sensory electrodes).

In some embodiments, the introducer drill may be operably coupled to a robotic system configured to control advancement and steering, or bending, of the introducer drill in a fully-automated or semi-automated manner. Fully-automated may mean without any physical user interaction (other than initiating the fully-automated procedure by starting a computer-executable program of stored instructions on a non-transitory storage medium) and semi-automated may mean that the movement is carried out by a user manipulating a controller (e.g., joystick) that directs or controls the robotic movement of the introducer drill.

Several embodiments of the invention have one or more of the following advantages: (i) increased treatment accuracy; (ii) increased efficacy and enhanced safety; (iii) increased efficiency as a result of fewer instruments to access and/or treat a target treatment location or ability to access vertebrae having differing bone anatomy or bone density; (iv) increased precision; (v) an integrated access and treatment instrument; (vi) ability to access locations in dense bone; and/or (vii) ease of use.

For purposes of summarizing the disclosure, certain aspects, advantages, and novel features of embodiments of the disclosure have been described herein. It is to be understood that not necessarily all such advantages may be achieved in accordance with any particular embodiment of the disclosure provided herein. Thus, the embodiments disclosed herein may be embodied or carried out in a manner that achieves or optimizes one advantage or group of advantages as taught or suggested herein without necessarily achieving other advantages as may be taught or suggested herein.

The methods summarized above and set forth in further detail below describe certain actions taken by a practitioner; however, it should be understood that they can also include the instruction of those actions by another party. For example, actions such as "applying thermal energy" include "instructing the applying of thermal energy." Further aspects of embodiments of the disclosure will be discussed in the following portions of the specification. With respect to the drawings, elements from one figure may be combined with elements from the other figures.

BRIEF DESCRIPTION OF THE DRAWINGS

Several embodiments of the disclosure will be more fully understood by reference to the following drawings which are for illustrative purposes only.

DETAILED DESCRIPTION

Figure 1:
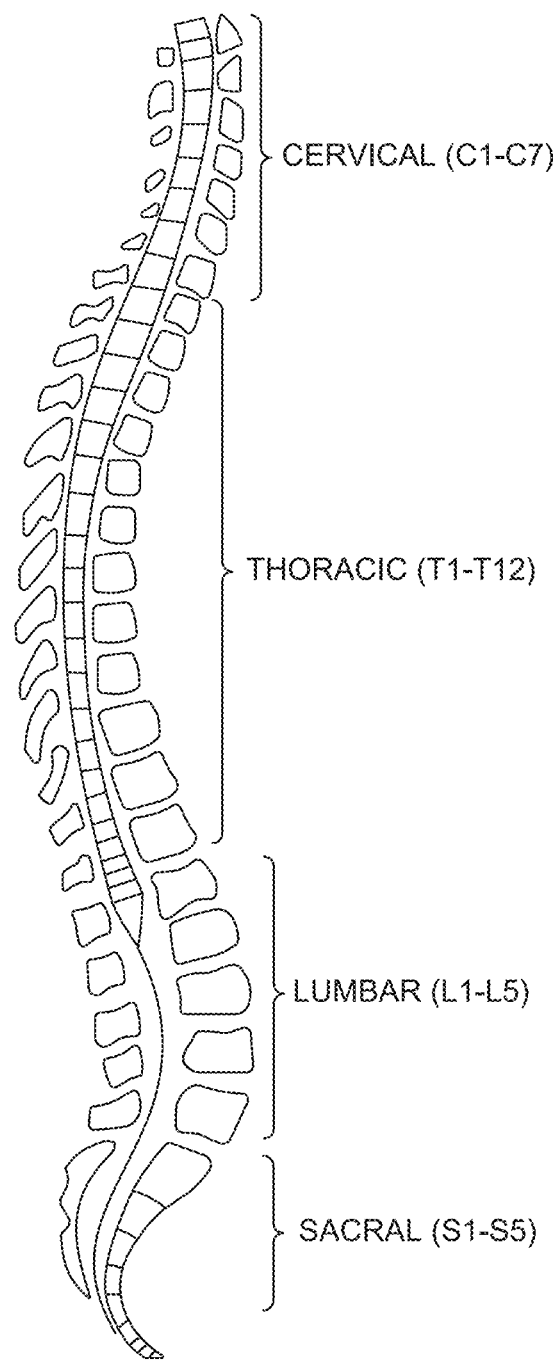
FIG. 1 illustrates various vertebral levels and vertebrae that may be treated by the systems, devices and methods described herein.

Several implementations described herein are directed to systems and methods for accessing target treatment and/or diagnostic locations within bone (e.g., a vertebral body). In some implementations, an intraosseous nerve (e.g., basivertebral nerve) within a bone (e.g., vertebral body) of the spine is accessed so as to facilitate treatment, or prevention of, back pain or other ailments or conditions associated with the spine (e.g., vertebral fractures, spinal tumors, scoliosis, spondylosis). The vertebral body may be located in any level of the vertebral column (e.g., cervical, thoracic, lumbar and/or sacral). FIG. 1 schematically illustrates a vertebral column and the various vertebral segments or levels. Multiple vertebral bodies may be accessed in a single visit or procedure (simultaneously with multiple instruments or sequentially with the same instrument or different instruments). The multiple vertebral bodies may be located in a single spine segment (e.g., two adjacent vertebral bodies in the sacral spine segment (e.g., S1 and S2) or lumbar spine segment (e.g., L3. L4 and/or L5) or thoracic spine segment or cervical spine segment) or in different spine segments (e.g., an L5 vertebra in the lumbar spine segment and an S1 vertebra in the sacral spine segment). Target treatment and/or diagnostic locations within bones other than vertebral bodies may also be accessed. For example, target locations within a humerus, radius, femur, tibia, calcaneus, tarsal bones, hips, knees, and/or phalanges may be accessed.

In accordance with several implementations, the systems and methods of accessing target treatment locations within bone described herein can be performed without surgical resection, without general anesthesia, without cooling, without performing vertebroplasty or injecting flowable material such as bone cement, and/or with virtually no blood loss. In accordance with several implementations, successful treatment can be performed in challenging or difficult-to-access locations and access can be varied depending on bone structure (e.g., differing bone mass density) or differing bone anatomy. One or more of these advantages also apply to access within bone outside of the spine (e.g., other orthopedic applications or other tissue).

In some embodiments, cooling may be optionally used to, for example, reduce an extent of heating within the bone or within a device that is generated by friction from rotation of a component of the device within the bone or by application of energy using the device.

Various methods of access may be used to access a vertebral body or other bone. In some implementations, the vertebral body is accessed transpedicularly (through one or both pedicles). In other implementations, the vertebral body is accessed extrapedicularly (e.g., without traversing through a pedicle). In some implementations, the vertebral body is accessed using an extreme lateral approach or a transforaminal approach, such as used in XLIF and TLIF interbody fusion procedures. In some implementations, an anterior approach is used to access the vertebral body.

Access tools used in conjunction with the introducer drill may include an introducer assembly including an outer cannula and a sharpened stylet, an inner cannula configured to be introduced through the outer cannula, and/or one or more additional stylets, curettes, or drills to facilitate access to an intraosseous location within a vertebral body or other bone. The access tools (e.g., outer cannula, inner cannula, stylets, curettes, drills) may have pre-curved distal end portions or may be actively steerable or curveable. Any of the access tools may have beveled or otherwise sharp tips or they may have blunt or rounded, atraumatic distal tips. Any of the access tools may be inserted in a minimally-invasive manner (e.g., percutaneously or laparoscopically).

In some implementations, an outer cannula assembly (e.g., introducer assembly) includes a straight outer cannula and a straight stylet configured to be received within the outer cannula. The outer cannula assembly may be inserted first to penetrate an outer cortical shell of a bone and provide a conduit for further access tools (e.g., steerable, or curveable, introducer drill) to the inner cancellous bone. An inner cannula assembly may include a cannula having a precurved or steerable distal end portion and a stylet having a corresponding pre-curved or steerable distal end portion. Multiple stylets having distal end portions with different curvatures may be provided in a kit and selected from by a clinician. The inner cannula assembly may alternatively be configured to remain straight and non-curved.

In accordance with several embodiments, a kit or system of access tools may include a steerable, or curveable, introducer drill. The steerable, or curveable, introducer drill may advantageously facilitate access to a target treatment location of a terminus of a basivertebral nerve located approximately mid-body in a vertebral body (e.g., approximately 30%-50% across the sagittal vertebral body width and in a posterior half of the vertebral body or encompassing a geometric center of the vertebral body) along a curved trajectory after using a transpedicular access approach. The steerable, or curveable, introducer drill may advantageously be used in hard bone.

Hard bone may be determined based on bone mass density testing, compressive strength determinations, compressive modulus determinations, imaging modalities, or based on tactile feel by the operator as access instruments are being advanced. In some implementations, hard bone may be determined as bone having a bone mineral density score within a standard deviation of a normal healthy young adult (e.g., a T score greater than or equal to −1). In some implementations, hard bone may be identified as bone having a compressive strength of greater than 4 MPa and/or a compressive modulus of greater than 80 MPa for cancellous bone and greater than 5.5 MPa and/or a compressive modulus of greater than 170 MPa for cortical bone. Hard bone may be defined as non-osteopenic bone or non-osteoporotic bone.

Figure 2:
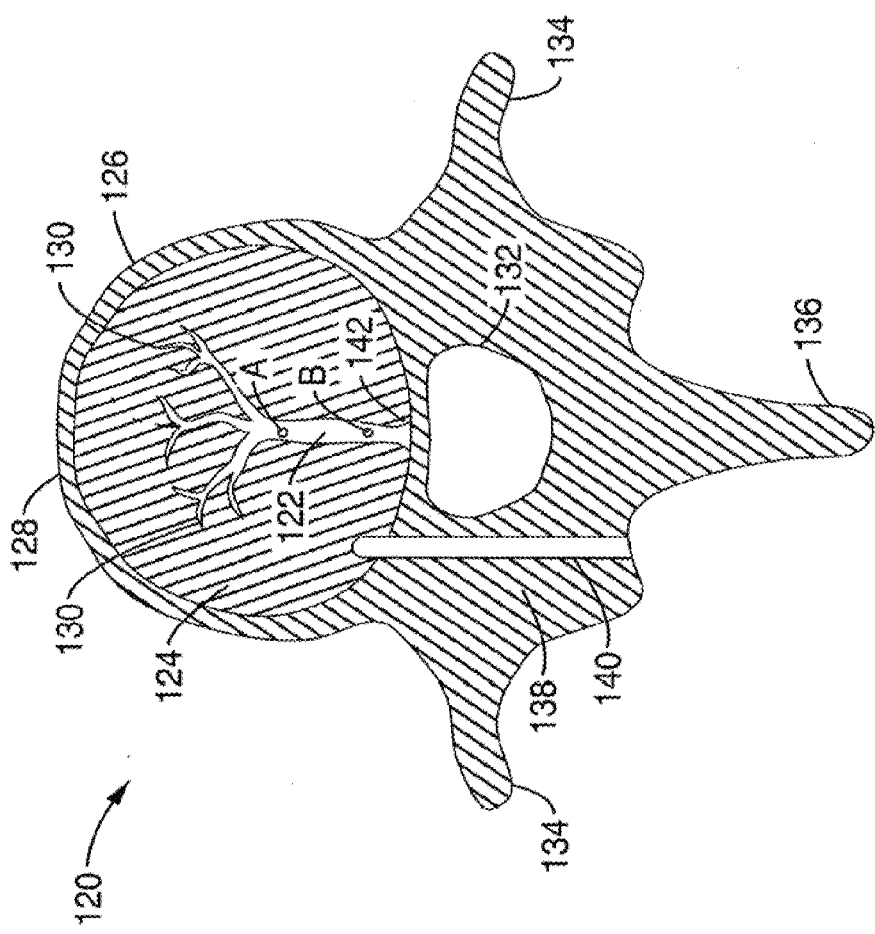
FIG. 2 illustrates a schematic representation of a vertebra having a basivertebral nerve.

FIG. 2 illustrates a cross-sectional view of a vertebra 120. The vertebra 120 includes a vertebral body 126, a vertebral foramen 132 posterior to the vertebral body 120, a transverse process 134 on each side of the vertebral foramen 132, a central spinous process 136 posterior to the vertebral foramen 132, and a pedicle 138 on each side of the vertebral foramen 132. The vertebral body 126 includes an inner cancellous bone region 124 and an outer cortical bone region 128. The vertebral body 126 also includes a basivertebral nerves 122. The basivertebral nerve 122 has at least one exit point 142 at a location along the basivertebral nerve 122 where the basivertebral nerve 122 exits the vertebral body 126 into the vertebral foramen 132. The basivertebral nerve 122 includes multiple branches 130 extending from a trunk or terminus throughout the cancellous bone region 124 of the vertebral body 126.

In accordance with several embodiments, a target treatment region to be accessed for modulation (e.g., ablation, denervation, stimulation) of the basivertebral nerve 122 is located within the cancellous bone region 124 at a location posterior to a terminus or trunk (labeled as point "A" in FIG. 2). In some embodiments, the target treatment region is not too close to the posterior border of the vertebral body 126. For example, the target treatment region may be at least 0.5 cm away (e.g., at least 1 cm away) from the posterior border (such as a distance away schematically represented by the point labeled "B" in FIG. 2). However, in other implementations, there is no posterior limit or boundary of the target treatment region. In accordance with several embodiments, the target treatment region to be accessed may be in a posterior half of the vertebral body 126 (e.g., posterior of the terminus or trunk of the basivertebral nerve). Treatment in this target treatment region may be advantageous because only a single portion of the basivertebral nerve 122 need be effectively treated to denervate or affect the entire system including the branches 130. The target treatment region may be located approximately mid-body in a vertebral body (e.g., approximately 30%-50% across the sagittal vertebral body width). The lateral-lateral center of the target treatment region may generally be aligned with the spinous process 136.

In one approach for accessing the basivertebral nerve, the patient's skin is penetrated with a surgical instrument which is then used to access the desired basivertebral nerves, i.e., percutaneously. In one embodiment, a transpedicular approach is used for penetrating the vertebral cortex to access the basivertebral nerve 122. A passageway 140 is created between one of the transverse processes 134 and the spinous process 136 through the pedicle 138 into the cancellous bone region 124 of the vertebral body 126 to access the target treatment region at or proximate to the terminus of the basivertebral nerve 122. In some vertebral bodies (e.g., vertebral bodies having hard bone or high-density bone or vertebral bodies at the lower lumbar levels or sacral levels) accessed transpedicularly, it may be difficult to obtain a curved trajectory to get to a desired target treatment region of the vertebral body 124 with instruments having pre-curved distal ends that are advanced through straight introducers and that cannot be actively steered or with straight access instruments. Accordingly, it may be advantageous according to several embodiments to include a steerable or curveable drill in a kit or system of access instruments to facilitate steeper curved trajectories to the targeted treatment region (for example, if the operator can tell that the density of the bone is going to be sufficiently dense or hard that additional steps and/or tools will be needed to obtain a desired curved trajectory to access a posterior portion (e.g., posterior half) of the vertebral body).

Figure 3:
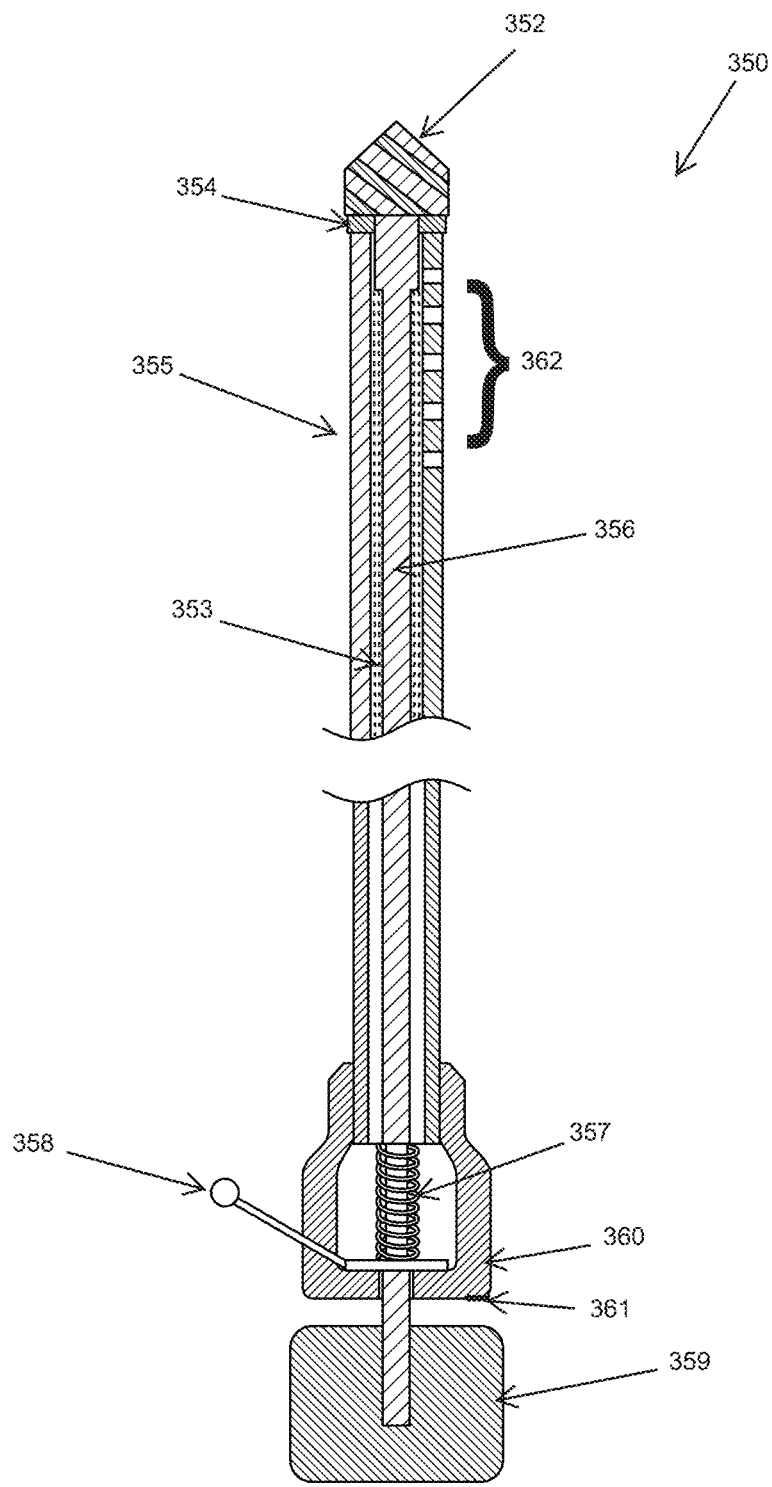
FIG. 3 illustrates an embodiment of an introducer drill.

FIG. 3 illustrates an embodiment of a steerable, or curveable, introducer drill 350 configured to access a desired target treatment location in bone (e.g., a vertebral body having hard or dense cancellous bone regions and/or a vertebral body in a spine region that may be difficult to access via a straight access tool, such as an L5, S1, or S2 vertebral body). For example, for a vertebral body, the desired target treatment location may be in a posterior half of the vertebral body 126 (e.g., posterior of the terminus or trunk of the basivertebral nerve 122) as described in connection with FIG. 2. In some implementations, the desired target treatment location may correspond to a geometric center of the vertebral body 126.

In accordance with several embodiments, the introducer drill 350 may comprise a single device configured to both penetrate a cortical outer shell of a bone along a straight trajectory and channel a path toward a target treatment location within an inner cancellous bone portion along a curved trajectory that can be adjusted or manipulated in real time. The illustrated embodiment of the drill 350 comprises a drill tip 352, a bushing 354, an outer tube 355, a drive shaft 356, a compression spring 357, an actuator 358, a rotational member 359, and a proximal housing 360. The illustrated drill tip 352 is pointed and includes top and/or side cutting flutes. The cutting flutes may have varying spacing, pitch, and widths as desired and/or required to facilitate bone drilling. A proximal end of the drill tip 352 is connected to the drive shaft 356. The drill tip 352 and drive shaft 256 may be made as a single integrated unitary component so as to prevent likelihood of separation or may comprise two separate components that are coupled or connected to each other during manufacturing (e.g., via welding, adhesive, and/or the like). The flutes may advantageously provide open volume for bone chips, fragments, or shards to be received therein. In some embodiments, the distal drill tip 352 is not a blade.

The bushing 354 is positioned between a proximal edge or surface of the drill tip 352 and a distal edge or surface of the outer tube 355. The bushing 354 may be adapted to guide, position and support the drive shaft 356 as it is rotated and curved, or bent, under compression and to protect the drive shaft 356 and pointed drill tip 352 from abrasion during bending and rotating. The drive shaft 356 may have a circular cross-sectional shape. The drive shaft 356 may have an elliptical cross-sectional shape. The bushing 354 may be made of steel or other high carbon metal or bronze or plastic (e.g., nylon). In some embodiments, the bushing 354 is substituted by or replaced with (or included in addition to) a thrust bearing and/or roller bearing. A thrust bearing (e.g., thrust ball bearing) may facilitate reduced wear on adjacent components and may help support axial loads. A roller bearing may include cylindrical- or barrel-shaped rolling elements as opposed to ball bearings to support loads (e.g., radial loads) and reduce friction. In some embodiments, the roller bearing comprises any cylindrical or spherical object that facilitates movement of and/or reduces wear from two adjacent components. The bushing 354 may cause rotation of the drive shaft 356 or may remain stationary with respect to rotation of the drive shaft 356.

The outer tube 355 concentrically and/or coaxially surrounds the drive shaft 356. A distal end portion 362 of the outer tube 355 comprises a segmented tube profile. The segmented tube portion 362 of the distal end portion of the outer tube 355 may include notches, slits, slots or apertures aligned on one side of the outer tube 355 and spaced apart and arranged so as to facilitate bending, steering, or articulating in a single, known, controlled direction. Accordingly, the outer tube 355 may advantageously bend or arc in one and only one lateral direction and such that the segmented tube portion 365 bends or arcs in a distal to proximal direction. The slots or slits may comprise transverse slots or slits. In other embodiments, the notches or slits or slots may be aligned on more than one side to facilitate bending in multiple directions (e.g., 2 opposite directions or omnidirectionally).

Figure 3A:
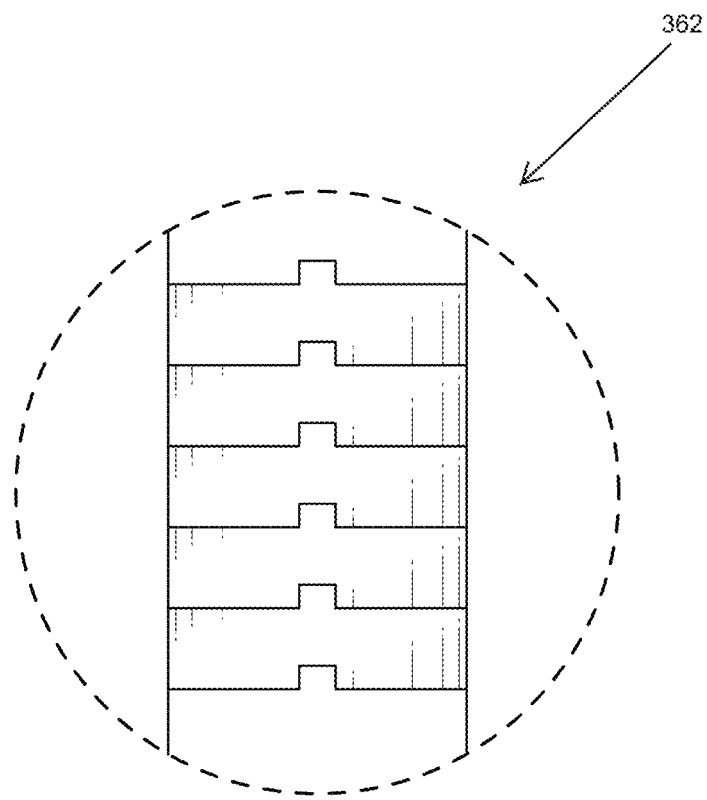
FIG. 3A is a side view of a distal end portion of the introducer drill of FIG. 3.

The proximal housing 360 of the outer tube 355 may include a visible indicator 361 (e.g., arrow head, marking) to indicate to the operator the single, known direction that the drill will bend or curve. A close-up side view of the segmented tube profile of the segmented tube portion 362 of the outer tube 355 is illustrated in FIG. 3A. The notches or slits or slots may be perpendicular or generally perpendicular to a central longitudinal axis of the outer tube 355 and may allow for adjacent segments to overlap or collapse on each other to facilitate bending of the outer tube 355. The number of, pitch, and spacing between the notches, slits, or slots may vary as desired and/or required. The length of the segmented tube portion 362 may also vary as desired and/or required. The outer tube 355 may be formed of nitinol material or another flexible metallic alloy or flexible shape-memory material. The outer tube 355 may be shape-set during manufacturing to remain in a straight configuration when in a default resting (or unconstrained) state or configuration, even once deployed from the constraint of an introducer cannula (not shown). In accordance with several embodiments, the outer tube 355 does not require multiple concentric tubes moving relative to each other, thereby reducing overall device diameter.

The compression spring 357 surrounds the drive shaft 356 and is mechanically coupled to the proximal end of the outer tube 355 and may be located within the housing 360 attached to the proximal end of the outer tube 355. The housing 360 may also include at least a portion of the actuator 358 operatively coupled to the drive shaft 356 that is adapted to add tension to or remove tension from the drive shaft 356. The actuator 358 may comprise a lever or other mechanism (e.g., pull wire assembly, slider, trigger, rotational member), adapted to add or remove tension to facilitate bending or curving of the segmented tube portion 362 of the outer tube 355, and thus the entire drill 350.

A pull wire assembly may include one or more pull wires extending from the proximal handle 360 to a distal end of the outer tube 355. The one or more pull wires may be tensioned to cause bending and relaxed to allow the outer tube 355 to straighten. The pull wires may provide axial force toward the proximal handle 360. The one or more pull wires may be adhered or welded to the distal end of the outer tube 355. A slider may be operably coupled to the segmented tube portion 362 such that sliding of the slide in one direction causes bending of the segmented tube portion 362 and sliding of the slider in the opposite direction causes straightening of the segmented tube portion 362. A trigger may be operably coupled to the segmented tube portion 362 such that actuation of the trigger (e.g., pressing or pulling the trigger) causes bending of the segmented tube portion 362 and releasing the trigger causes straightening of the segmented tube portion 362. A rotational member (e.g. thumb or finger wheel, crank, or knob) may be operably coupled to the segmented tube portion 362 such that rotation of the rotational member in a first rotational direction (e.g., clockwise) causes bending of the segmented tube portion 362 and rotation of the rotational member in an opposite rotational direction (e.g., counter-clockwise) causes straightening of the segmented tube portion 362. In some implementations, the slider, trigger, or rotational member may be used in conjunction with a pull wire assembly.

The proximal end of the drive shaft 356 is mechanically coupled to the rotational paddle 359 or other structural member adapted to be acted upon to cause rotation of the drive shaft 356. The rotational member 359 may comprise a paddle, wheel, crank, knob, handle, enlarged tip, or other structure adapted to be rotated manually by an operator (e.g., a clinician or surgeon) or automatically (e.g., via a motor of a robotic system) without manual operator contact. In some embodiments, the drive shaft 356 does not have a lumen and does not include a stiffening wire adapted for insertion within the lumen of the drive shaft. In some embodiments, the drive shaft has a lumen to facilitate introduction or circulation of cooling fluid via closed loop fluid circulation system.

The drill 350 may be initially inserted into bone (e.g., a vertebral body) through an introducer cannula (not shown) in a default straight configuration with no tension applied on the drive shaft 356. The insertion may be performed while rotating the rotational member 359. Because the outer tube 355 is shape set in a straight configuration, the drill 350 should naturally hold this straight configuration even when unconstrained. Once the drill tip 352 has been initially inserted into the bone (e.g., vertebral body), the actuator 358 may be actuated to provide tension on the drive shaft 356, which causes compression on the segmented tube portion 362 of the outer tube 355. This action causes the drill 350 to attempt to collapse the segments of the segmented tube portion 362 of the outer tube 355 and lean (e.g., bend, arc, steer, or articulate) into a curved shape (e.g., in a distal-to-proximal configuration). The compression spring 357 takes up lateral forces that are unable to be used to curve the drill 350 (such as because the drill 350 is constricted in an introducer cannula or in hard, high-density bone). The fully curved angle may be in a range between 20 degrees and 90 degrees (e.g., between 20 degrees and 60 degrees, between 40 degrees and 70 degrees, between 30 degrees and 80 degrees, between 35 degrees and 75 degrees, between 50 degrees and 90 degrees, between 30 degrees and 70 degrees, between 45 degrees and 65 degrees, overlapping ranges thereof, or any value within the recited ranges).

In some embodiments, the drill 350 may optionally include a second tube 353 (e.g., inner tube) attached (e.g., welded or bonded) to the distal end of the drive shaft 356. The second tube 353 is illustrated with dotted lines in FIG. 3. The second tube 353 may be used to apply compression to the outer tube 355 and force the outer tube 355 to bend or arc. In accordance with several embodiments, inclusion of the second tube 353 (e.g., inner tube) may allow the drive shaft 356 to solely function for the drill function (e.g., transmitting torque to the drill tip) and not for both drilling and application of compression to the outer tube 355. The second tube 353 (e.g., inner tube) may be formed of nitinol material or another flexible metallic alloy or flexible shape-memory material (e.g., similar to the outer tube 355). The second tube 353 may extend from the drill tip 352 and extend along any length or portion of the outer tube 355. For example, the second tube 353 may extend to just cover the segmented tube portion 362 or may extend to the proximal handle 360 or may extend proximal to the segmented tube portion 362 but distal to the proximal handle 360. The second tube 353 may or may not include a segmented tube portion corresponding to the segmented tube portion 362 of the outer tube 355. The inner tube 353 may advantageously apply compression to the outer tube 355 without compromising the structural integrity of the drive shaft 356 (such as by requiring an internal lumen in the drive shaft for insertion of a stiffening element for imparting rigidity). In some embodiments, the drill 350 does not include any components configured for insertion through the drive shaft 356.

The drill 350 may then either be manually advanced forward with axial pressure while the drive shaft 356 is rotated or an automated separate mechanism (such as a robotic surgical system) can provide the axial pressure. As the drill 350 advances within the bone, the drill 350 moves forward and reduces its radius of curvature as it is deployed (and as a result, the compression spring 357 relaxes). The actuator 358 may be adjusted to adjust the radius of curvature during advancement. The radius of curvature may be actively controlled and monitored under visualization. In accordance with several embodiments, advancement may be performed while using fluoroscopy or other imaging modalities to facilitate access along a desired trajectory to the desired target treatment and/or diagnostic location.

Once fully deployed, the actuator 358 can be caused to relieve tension on the drive shaft 356, thereby allowing the outer tube 355 to straighten as the drill 350 is removed from the bone (e.g., vertebral body). This straightening may advantageously help prevent, or reduce the likelihood of, the segments of the segmented tube portion 362 of the outer tube 355 from catching on the introducer cannula as force is applied on the opposite side of the outer tube 355. In some embodiments, the compression spring 357 may be replaced with a hydraulic or pneumatic mechanism. The hydraulic or pneumatic mechanism may serve to provide a similar function as the mechanical compression spring 357.

Figure 4:
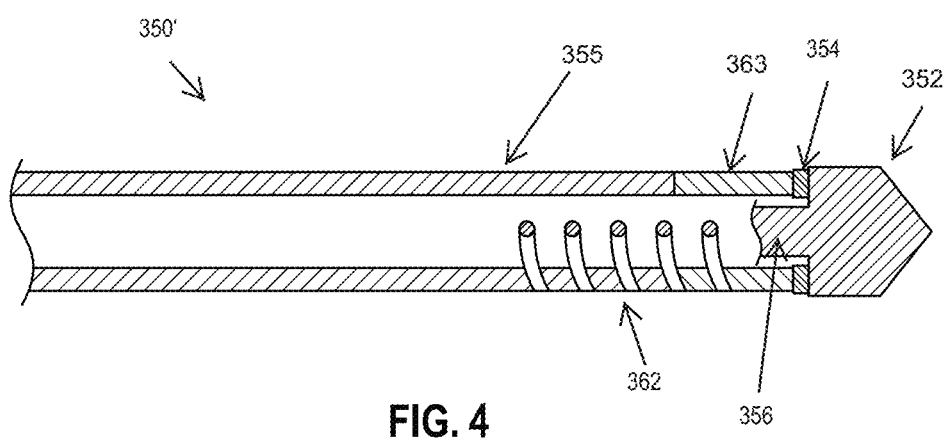
FIG. 4 is a partial cross-section side view of a distal end portion of another embodiment of an introducer drill.

FIG. 4 illustrates an alternative design of a distal end portion that could optionally be incorporated into the steerable drill 350 of FIG. 3. In this embodiment, the drill 350' may advantageously function as both an access instrument and a treatment instrument. In this embodiment, the drill tip 352 could function as a distal electrode of a bipolar electrode pair and a conductive portion 363 of the outer tube 355 may function as a proximal electrode of the bipolar electrode pair, with proper masking or electrical isolation being achieved by appropriate insulation structures or materials positioned between the distal electrode and proximal electrode portions. In one implementation, at least a portion of the outer tube 355 (e.g., a portion proximal of the conductive portion 363) could be coated with a conformal, anodized, and/or other non-electrically conductive coating to help with surface friction and concentrated electrode operation. The outer tube 355 could be masked to provide a 4×2×4 mm electrode spacing or other suitable electrode spacing geometry. In some embodiments, the bushing 354 may function as an insulator between the conductive portion 363 of the outer tube 355 and the drill tip 352.

The drill tip 352 may or may not include cutting flutes. A distal end portion of the outer tube 355 of the drill 350' may include the segmented tube portion 362 described in connection with FIGS. 3 and 3A.

The drill 350 may include one or more electrical leads or wires electrically coupled between a connector adapted to electrically interface with a radiofrequency generator and the drill tip 352 so as to allow for the drill 350 to deliver radiofrequency energy sufficient to modulate (e.g., ablate, stimulate, denervate) tissue (e.g., bone tissue, nerves, tumor tissue). For example, the drill 350 may advantageously be used to both access a desired target treatment location within bone and ablate nerves or tumors within the bone.

Applying ablative radiofrequency energy to the target treatment location within the bone may be performed according to the following example treatment parameters: a frequency between 400 kHz and 600 kHz (e.g., between 400 kHz and 500 kHz, between 450 kHz and 500 kHz, between 470 kHz and 490 kHz, between 500 kHz and 600 kHz, overlapping ranges thereof, or any value within the recited ranges); a target temperature of between 60 degrees Celsius and 90 degrees Celsius (e.g., between 60 degrees Celsius and 80 degrees Celsius, between 65 degrees Celsius and 75 degrees Celsius, between 70 degrees Celsius and 80 degrees Celsius, between 80 degrees Celsius and 90 degrees Celsius, overlapping ranges thereof, 70 degrees Celsius, 75 degrees Celsius, 80 degrees Celsius, 85 degrees Celsius, 90 degrees Celsius or any other value within the recited ranges); a temperature ramp of between 0.5 and 3 degrees Celsius per second (e.g., 0.5 degree Celsius per second, 1 degree Celsius per second, 1.5 degrees Celsius per second, 2 degrees Celsius per second, 2.5 degrees Celsius per second, 3 degrees Celsius per second); and an active energy delivery time of between 1 minute and 20 minutes (e.g., between 1 minute and 5 minutes, between 2 minutes and 10 minutes, between 4 minutes and 8 minutes, between 5 minutes and 10 minutes, between 5 minutes and 15 minutes, between 10 minutes and 20 minutes, overlapping ranges thereof, 5 minutes, 10 minutes, 12, minutes, 14 minutes, 15 minutes, 16 minutes, 18 minutes, 20 minutes, or any value within the recited ranges).

In some implementations, a target ablation zone has a major diameter along a long axis of between 20 mm and 30 mm and a minor diameter along a short axis of between 5 mm and 15 mm. In some implementations, the target ablation zone generally comprises a 1 cm sphere. The lesion may form an elliptical shape or other controlled lesion shape as desired and/or required.

In some implementations, no active cooling is provided. In other implementations, cooling fluid may be circulated through one or more internal lumens surrounding the drive shaft 356. The drill 350' may include one or more temperature sensors (e.g., thermocouples, thermistors) configured to monitor temperature at one or more locations along the drill 350'. The drills 350, 350' may include one or more sensors configured to provide stimulation to sense a presence or location of nerves within bone (e.g., basivertebral nerve within a vertebral body or nerves adjacent a pedicle of a vertebra).

In some implementations, the drill 350' is configured to operate as a monopolar electrode. For example, an electrical lead may only be coupled to the conductive portion 363 and not to the drill tip 352 and a ground pad may be used as the second electrode. The drill 350 may additionally or alternatively be used to provide stimulation energy to facilitate confirmation of nerve ablation or to help identify locations of nerves within the bone to facilitate identification of the desired target treatment region.

In some implementations, the steerable drill comprises various features that are present as single features (as opposed to multiple features). For example, in one embodiment, the drill includes a single electrode. A single thermocouple (or other means for measuring temperature) may also be included. Multiple features or components are provided in alternate embodiments.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Further, the disclosure (including the figures) herein of any particular feature, aspect, method, property, characteristic, quality, attribute, element, or the like in connection with various embodiments can be used in all other embodiments set forth herein. Any section headings used herein are merely provided to enhance readability and are not intended to limit the scope of the embodiments disclosed in a particular section to the features or elements disclosed in that section.

While the embodiments are susceptible to various modifications, and alternative forms, specific examples thereof have been shown in the drawings and are herein described in detail. It should be understood, however, that the embodiments are not to be limited to the particular forms or methods disclosed, but to the contrary, the embodiments are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

The terms "top," "bottom," "first." "second." "upper." "lower," "height." "width." "length," "end," "side," "horizontal," "vertical," and similar terms may be used herein; it should be understood that these terms have reference only to the structures shown in the figures and are utilized only to facilitate describing embodiments of the disclosure. Various embodiments of the disclosure have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from 20 to 90 degrees should be considered to have specifically disclosed subranges such as from 20 to 40 degrees, from 30 to 60 degrees, from 45 to 75 degrees, from 80 to 90 degrees etc., as well as individual numbers within that range, for example, 20, 30, 40, 45, 90, 40.5, 60.5 and any whole and partial increments therebetween. Language such as "up to," "at least," "greater than," "less than," "between," and the like includes the number recited. Numbers preceded by a term such as "about" or "approximately" include the recited numbers. For example, "approximately 30-50%" includes 30% and 50%. The terms "generally" and "substantially" as used herein represent an amount close to the stated amount that still performs a desired function or achieves a desired result.

What is claimed is:

1. A curveable introducer drill configured to access a target treatment region within hard bone along a curved trajectory, the drill comprising:
    a drive shaft comprising a proximal rotational paddle, a distal drill tip, and an elongate shaft portion extending from the proximal rotational paddle to the distal drill tip,
    wherein the distal drill tip is pointed and comprises top and side cutting flutes;
    an outer tube surrounding the drive shaft, the outer tube comprising a proximal housing at its proximal end,
    wherein the outer tube comprises a shape memory material that is shape set to have a straight configuration when unconstrained,
    wherein the proximal rotational paddle extends out of a proximal end of the proximal housing of the outer tube;
    wherein one and only one side of a distal end portion of the outer tube comprises a segmented tube section comprised of tube segments and slits configured to facilitate controlled bending of the segmented tube section of the outer tube in a single known direction;
    a lever operably coupled to the drive shaft and adapted to apply tension to the drive shaft which, in turn, exerts a lateral force on the segmented tube section of the outer tube to cause the controlled bending of the segmented tube section in the single known direction;
    a compression spring mechanically coupled to a proximal end of the outer tube; and
    a bushing positioned between a distal edge of the outer tube and a proximal edge of the distal drill tip.

2. The drill of claim 1, wherein the outer tube comprises a shape memory material that is shape set to have a straight configuration when unconstrained.

3. The drill of claim 1, wherein the proximal housing of the outer tube comprises an indicator configured to indicate the single known direction.

4. The drill of claim 1, further comprising an inner tube within the outer tube and surrounding the drive shaft, wherein the inner tube is attached to the distal end of the drive shaft, and wherein the inner tube is configured to apply compression to the outer tube and force it to apply lateral force.

5. The drill of claim 1, wherein the distal drill tip is configured to form a distal electrode of a bipolar electrode pair and a conductive portion of the outer tube is configured to form a proximal electrode of the bipolar electrode pair.

6. The drill of claim 5, further comprising at least one electrically conductive wire coupled between the distal drill tip and a radiofrequency generator.

7. The drill of claim 1, wherein at least a portion of the outer tube comprises a non-electrically conductive coating.

8. The drill of claim 1, further comprising one or more sensors configured to sense a presence or location of nerves within bone.

9. A steerable introducer drill comprising:
a drive shaft comprising a proximal rotational member and a distal drill tip;
an outer tube surrounding the drive shaft, the outer tube comprising a proximal housing and a distal end portion, wherein the distal end portion includes a segmented tube section configured to facilitate controlled bending;
an actuator operably coupled to the drive shaft and adapted to apply tension to the drive shaft to cause the segmented tube section to bend;
a lever operably coupled to the actuator to control the tension applied to the drive shaft; and
a bushing positioned between a distal edge of the outer tube and a proximal edge of the distal drill tip.

10. The drill of claim 9, wherein the outer tube comprises a shape memory material that is shape set to have a straight configuration when unconstrained.

11. The drill of claim 9, wherein the proximal housing of the outer tube comprises an indicator configured to indicate a direction of bending of the segmented tube section.

12. The drill of claim 9, further comprising an inner tube within the outer tube and surrounding the drive shaft, wherein the inner tube is coupled to a distal end of the drive shaft, and wherein the inner tube is configured to apply compression to the outer tube to facilitate bending of the segmented tube section.

13. The drill of claim 9, wherein the distal drill tip comprises top and side cutting flutes.

14. The drill of claim 9, wherein the actuator is configured to apply tension to the drive shaft to cause the segmented tube section to bend in a single known direction.

15. The drill of claim 9, further comprising a compression spring mechanically coupled to a proximal end of the outer tube.

16. The drill of claim 9, wherein the distal drill tip is configured to form a distal electrode of a bipolar electrode pair and a conductive portion of the outer tube is configured to form a proximal electrode of the bipolar electrode pair.

* * * * *